(12) United States Patent
Monroy Samperi

(10) Patent No.: US 11,077,402 B2
(45) Date of Patent: Aug. 3, 2021

(54) SYSTEM FOR THE CAPTURE AND MONITORING OF ATMOSPHERIC POLLUTING AGENTS

(71) Applicant: Carlos Monroy Samperi, Veracruz (MX)

(72) Inventor: Carlos Monroy Samperi, Veracruz (MX)

(*) Notice: Subject to any disclaimer, the term of this patent is extended or adjusted under 35 U.S.C. 154(b) by 332 days.

(21) Appl. No.: 16/304,400

(22) PCT Filed: Nov. 22, 2017

(86) PCT No.: PCT/MX2017/000134
§ 371 (c)(1),
(2) Date: Nov. 26, 2018

(87) PCT Pub. No.: WO2018/208139
PCT Pub. Date: Nov. 15, 2018

(65) Prior Publication Data
US 2019/0176086 A1  Jun. 13, 2019

(30) Foreign Application Priority Data

May 8, 2017  (MX) .................... MX/a/2017/005956

(51) Int. Cl.
*B01D 53/84* (2006.01)
*B01D 53/34* (2006.01)
(Continued)

(52) U.S. Cl.
CPC ............ *B01D 53/84* (2013.01); *B01D 47/00* (2013.01); *B01D 47/02* (2013.01); *B01D 53/34* (2013.01);
(Continued)

(58) Field of Classification Search
CPC ...... B01D 53/84; B01D 53/34; B01D 53/346; B01D 47/00; B01D 47/02; B01D 2251/95;
(Continued)

(56) References Cited

U.S. PATENT DOCUMENTS

| 6,896,804 B2 * | 5/2005 | Haerther | ................. C02F 3/327 210/602 |
| 7,708,806 B2 * | 5/2010 | Wright | .................... B01J 41/05 95/139 |

(Continued)

FOREIGN PATENT DOCUMENTS

| FR | 2945215 | 11/2010 |
| WO | WO9927351 | 6/1999 |

(Continued)

*Primary Examiner* — Michael L Hobbs
*Assistant Examiner* — Lenora A Abel
(74) *Attorney, Agent, or Firm* — Defillo & Associates, Inc.; Evelyn A Defillo

(57) ABSTRACT

A system for capturing and monitoring atmospheric polluting agents (1) that includes a protection skeleton (100) that covers and protects the entire system; a power supply module (200) for providing electrical energy to the system; a bioremediation module (300) that captures and bioremediates the polluted gaseous streams that circulate inside it; a control and monitoring module (400), which census and modifies the operation parameters in real time and at least one particle capture unit (500) that gathers the particles that approach the system. The system boosts the restoration of polluted gaseous streams with a certain concentration of some substance that could represent a risk for the health of the people.

18 Claims, 25 Drawing Sheets

(51) Int. Cl.
    *B03C 3/017*     (2006.01)
    *C12M 1/00*     (2006.01)
    *C12M 1/34*     (2006.01)
    *B01D 47/02*     (2006.01)
    *B01D 47/00*     (2006.01)
    *H01M 10/46*     (2006.01)

(52) U.S. Cl.
    CPC ............ *B01D 53/346* (2013.01); *B03C 3/017* (2013.01); *C12M 23/58* (2013.01); *C12M 41/12* (2013.01); *C12M 41/26* (2013.01); *B01D 2251/95* (2013.01); *H01M 10/465* (2013.01); *H01M 2220/10* (2013.01)

(58) Field of Classification Search
    CPC ....... B03C 3/017; C12M 23/58; C12M 41/12; C12M 41/26; H01M 10/465; H01M 2220/10
    USPC ...................................................... 435/286.1
    See application file for complete search history.

(56) References Cited

U.S. PATENT DOCUMENTS

| | | | |
|---|---|---|---|
| 8,329,460 B2* | 12/2012 | Parent | .................... B01D 53/85 435/299.1 |
| 2002/0061270 A1 | 5/2002 | Osborne | |
| 2003/0213745 A1 | 11/2003 | Haerther | |
| 2015/0143806 A1* | 5/2015 | Friesth | .................... F24S 25/50 60/517 |

FOREIGN PATENT DOCUMENTS

| | | |
|---|---|---|
| WO | WO20070047805 | 4/2007 |
| WO | WO2009002772 | 12/2008 |

* cited by examiner

SYSTEM FOR THE CAPTURE AND MONITORING OF ATMOSPHERIC POLLUTING AGENTS

CROSS REFERENCE TO RELATED APPLICATION

This application is a national stage entry of PCT/MX2017/000134 filed Nov. 22, 2017, under the International Convention claiming priority over Mexican Patent Application No. MX/a/2017/005956 filed May 8, 2017.

TECHNICAL FIELD

This invention belongs to the field of diverse industrial techniques. Particularly, it belongs to the field of devices and processes for the separation, capture and/or the removal of air particles, gases and vapors. Even more specifically, it refers to a system for capturing and monitoring atmospheric polluting agents.

BACKGROUND

Air pollution is an environmental problem that has increased during the last years, especially in large cities. It is widely known that the emission and dispersion of pollutants in the atmosphere, is the result of atrophic activities, in which topography and weather conditions contribute significantly. Before this issue, many countries have implemented actions in order to diminish the production of atmospheric pollutants. For instance, the "Kyoto protocol" is an agreement signed by several industrialized and developing countries in Dec. 11, 1997 to boost sustainable development. The countries that joined the treaty are obliged to accomplish the quantified commitments of limitation and reduction of emissions, making and applying public policies and conformity measures to their national circumstances. The members of the agreement are committed to reduce their Green House Gases (GHS) by 5% concerning their emissions in the base year (1990), from 2005 to 2012. The regulation of pollution from vehicles is one of the implemented measures, which has had successful outcomes for the reduction of three pollutants that are part of the group defined as "criteria pollutants" by the United States Environment Protection Agency (USEPA): Lead (Pb), Carbon Monoxide (CO) and Sulfur Dioxide (SO2). However, the air quality limits allowed for other contaminants are exceeded even more frequently. Because of this, there have been proposals of technologies to diminish the polluting emissions issued by vehicles. The American U.S. Pat. No. 6,866,756 (B2), describes a hydrogen generator to be used in the fuel system of vehicles, which has an electrolyser for the electrolysis of water into a gaseous mixture of hydrogen and oxygen. The electrolyser is adapted to supply this mixture in the fuel system of an internal combustion engine. Another well-known invention is the one described in detail in the request US 2014/0150737 (A1). It refers to a catalyzer device for hydraulic systems of internal combustion engines that produces hydrogen as positive catalyzer for an internal combustion engine. The hydronic catalyzer device uses an electrolysis unit and an electric current source. The electrolysis unit includes a water container and a hydrogen/oxygen separator in order to define an oxygen chamber and a hydrogen chamber inside the water recipient, a hydrogen output for the connection between the hydrogen chamber and the internal combustion engine, and an oxygen duct for the ventilation of the oxygen chamber to the atmosphere.

Likewise, there is knowledge about several technologies, which provide a solution to the presented problem within this technical field. We could quote the following: US20030085135 (A1), US 20140373509 (A1), U.S. Pat. No. 1,905,627 (A), U.S. Pat. No. 2,140,254 (A), U.S. Pat. No. 4,480,595 (A), US 20030085135 (A1), US 20080241033 (A1), US 20080241033 (A1), US 20100242928 (A1), US 20110283960 (A1), US 20140020365 (A1), US 20120240557 (A1), and US 20110302909 (A1). However, the latter inventions only give solution for the pollutants coming from vehicles. Therefore, it is still necessary to look for alternatives for the atmospheric pollutants produced by other sources.

Some alternatives to reduce air pollution in cities are the "ecotechnologies". Just to quote one of them, the "vertical gardens", which intend to provide benefits for the environment, are becoming into an ecological trend within the field of the "Green constructions", having great success and acceptation in architecture. An example for this case, is given in the international request WO 2014084702 (A1), which describes an ecological building system for edifications with green walls for the construction of any kind of property, including cultivation and plant growing. The system consists in a set of polygonal modules, which when put together integrate the main supporting structure for plant growing. There are other technologies within the same field in the requests: WO 2011117437 (A1), ES 1046000 (U), ES 2317293 (T3), U.S. Pat. No. 4,295,296 (A1), ES 2101652 (A1), JP 2004076307 (A), CN 201053150 (A), CN 2494856 (A), and JP 2008267684 (A). However, the latter intend to provide structures whose application is ornamental and aesthetic, that is to say, even though the biological function of the plants contributes to favor the environment around the "green walls" structure where they are, it is not enough to reduce atmospheric pollutants. On the contrary, if weather conditions are not favorable, the plants die.

In this way, the need to find a solution to reduce atmospheric pollution prevails, mainly throughout urban zones and outdoor public places. Among the current technology proposals that have risen to this end, we consider those known as "Urban trees", as the closest to the present invention. Just to give an instance, the Chinese patent CN 103982061 (B) describes a devise for bus, which is supplied by photovoltaic energy, and has the purpose to purify the air. The latter belongs to the technical field of applications to protect the environment. The invention works with an electric current that is produced by a solar cell, stored by an energy storage battery and transmitted to a current controller through an electric cable. Air gets into an electrostatic device in order to ionize the powder in an ionization chamber. Once particulate matters (powder) are charged, they tend to an adsorption chamber under the effects of an electric field force. Finally, the air stream and the purified air are discharged within the surrounding environment.

Another example is in the request of the Chinese patent CN 103982061(B). It describes an air purifier smart artificial tree that accounts with photovoltaic materials as energy source. The system has a transformer substation, a water supply station and powder removal automatic devices. The latter devices are uniformly disposed in intervals at the sides of a city road. All the powder removal devices are connected in parallel each other through cables and to the transformer substation. They are also connected each other by mean of water supply pipelines, and finally, they are linked to the water supply station. In the same way, the Chinese utility model requests CN 203193547 (U), CN 203862388 (U) and CN 204593690 (U) depict pollutant particles collector devices. However, any of these documents consider the possibility of implementing the use of microalgae as a medium for the depuration and/or bioremediation of air.

Those known as "Urban Trees" can be found in some websites. The designers Mario Caceres and Christian Canonicoa have proposed a system capable of taking CO2 from the air in order to transform it into oxygen to be then expelled out again. Just exactly as the photosynthesis of natural trees.

Finally, it is worth mentioning the patent requests of the American inventor Klaus Lackner, who has provided several inventions related to the field of Carbon Dioxide capture technologies. Among his newer publications, it is the international request WO 2016164563 (A1), which refers to both, a system and a method that use one or more CO2 absorbent substrates and an oscillation cycle. For instance, the humidity oscillation cycle can be used for increasing the partial pressure of the CO2 in an inlet valve, just as a membrane carbonization photobioreactor. We could mention many other inventions, such as: WO 2016164781 (A1), US 2016207037 (A1), US 2015274536 (A1), US2015167432 (A1), US2015165373 (A1), US 2014370576 (A1), U.S. Pat. No. 9,387,433 (B2), U.S. Pat. No. 9,266,051 (B2), U.S. Pat. No. 8,702,847 (B2), U.S. Pat. No. 8,435,327 (B2), WO 2012058662 (A2), US 2012058032 (A1), US 2011293503 (A1) US2011203311 (A1), US 2011203174 (A1), U.S. Pat. No. 8,999,279 (B2), and US 2011108421 (A1). However, neither of the latter publications describes nor suggests the technical features of the present invention.

Derived from the quoted state of the technique, it is evident that, even though nowadays there are well known both, devices and systems for the capture of air pollutants with microorganisms, there is no knowledge about the required specific conditions to keep their viability and stability in variable environments. Particularly in outdoor spaces and cities with high atmospheric pollution index, where parameters such as light, nutrients, pH, temperature and CO2, among others, make the functionality of the microorganisms difficult, by causing them the death.

This represents a problem due to the environmental conditions of outdoor places such as streets, parks and squares can significantly change any time now, or they are simply not the same throughout the year, which causes the wrong (or null) working of the device/system. Therefore, our intention is providing an alternative for the capture of atmospheric pollutants, using bioremediation microorganisms such as microalgae and/or cyanobacteria, which are able to operate efficiently in outdoor spaces, where capturing atmospheric pollutants is mainly required.

BRIEF DESCRIPTION OF THE INVENTION

Therefore, the system for capturing and monitoring atmospheric polluting agents (1) is a protection object, which comprehends a protection skeleton (100) that covers and protects the entire system; a power supply module (200), which intends to provide electrical energy to the system; a gases bioremediation module (300), which has the function of capturing and bioremediating the gaseous polluted streams that circulate inside it; a control and monitoring module (400), which census and modifies the operation parameters in real time; at least one particles capture unit (500), which gathers the particles that approach the system in its interior.

The gases bioremediation module (300) has at least one polluted streams purifier bioreactor (315) circumferentially disposed; a power supply module, which provides electrical energy to the components of the polluted streams purifier bioreactor (315) and a base module (316) at the bottom part, which intends to be the supporting structure to give stability. The liquid containment module (317) has the purpose of storing the medium/nutritive solution that requires a variety of microalgae/cyanobacteria to grow. The streams exchange module (318) is able to provide the elements to allow a stream (with a certain level of pollution) to be displaced inside the polluted streams purifier bioreactor (315), by having an exchange of the mentioned pollutant elements. It also has a module for capturing gaseous streams (319), which is where the polluted streams introduced from the exterior are treated. Furthermore, the control module (320) serves to control several functions of the polluted streams purifier bioreactor (315).

The liquid contention module (317) is mainly compounded by a storage tank (322) that contains a nutritive solution, so as a hydraulic pump (324) to boost the nutritive solution to the interior of the main tank (325) by mean of a plurality of drill holes located on its periphery. Moreover, there is a streams exchange module (318), which has a streams exchanger cylinder (331) along the axial axe of the main tank (325). The cylinder has a transversal section (preferably circular) with an internal void (332) along the entire axial axe. Moreover, a plurality of bottomless drill holes (333), which are located in a zone next to the top part of the streams exchanger cylinder (331), allow to constantly keeping a nutritive solution at the same level than them, for when the latter falls into the internal void (332). This happens because there is a constant recirculation of the nutritive solution caused by the hydraulic pump (324) towards the top part of the main tank (325).

A second protection object refers to a polluted streams purifier bioreactor (315) compounded by a power supply module, which provides electrical energy to the components of the polluted streams purifier bioreactor (315), and a base module (316) at the bottom part, which intends to be the supporting structure to give stability. The liquid containment module (317) has the purpose of storing the medium/ nutritive solution that requires a variety of microalgae/ cyanobacteria for its growth. The streams exchange module (318) is able to provide the elements to allow a stream (with a certain level of pollution) to be displaced inside the polluted streams purifier bioreactor (315), by having an exchange of the mentioned pollutant elements. It also has a module for capturing gaseous streams (319), which is where the polluted streams introduced from the exterior are treated. The control module (320) serves to control several functions of the polluted streams purifier bioreactor (315).

The liquid contention module (317) is mainly compounded by a storage tank (322) that contains a nutritive solution, so as a hydraulic pump (324) to boost the nutritive solution to the interior of the main tank (325) by mean of a plurality of drill holes located on its periphery. Moreover, there is a streams exchange module (318), which has a streams exchanger cylinder (331) along the axial axe of the main tank (325). The cylinder has a transversal section (preferably circular) with an internal void (332) along the entire axial axe. Moreover, a plurality of bottomless drill holes (333), which are located in a zone next to the top part of the streams exchanger cylinder (331), allow to constantly keeping a nutritive solution at the same level than them, for when the latter falls into the internal void (332). This happens because there is a constant recirculation of the nutritive solution caused by the hydraulic pump (324) towards the top part of the main tank (325).

BRIEF DESCRIPTION OF THE FIGURES

FIG. 16-B shows a sectioned view of section A-A of FIG. 16-A.

DESCRIPTION OF THE INVENTION

Figure 1:
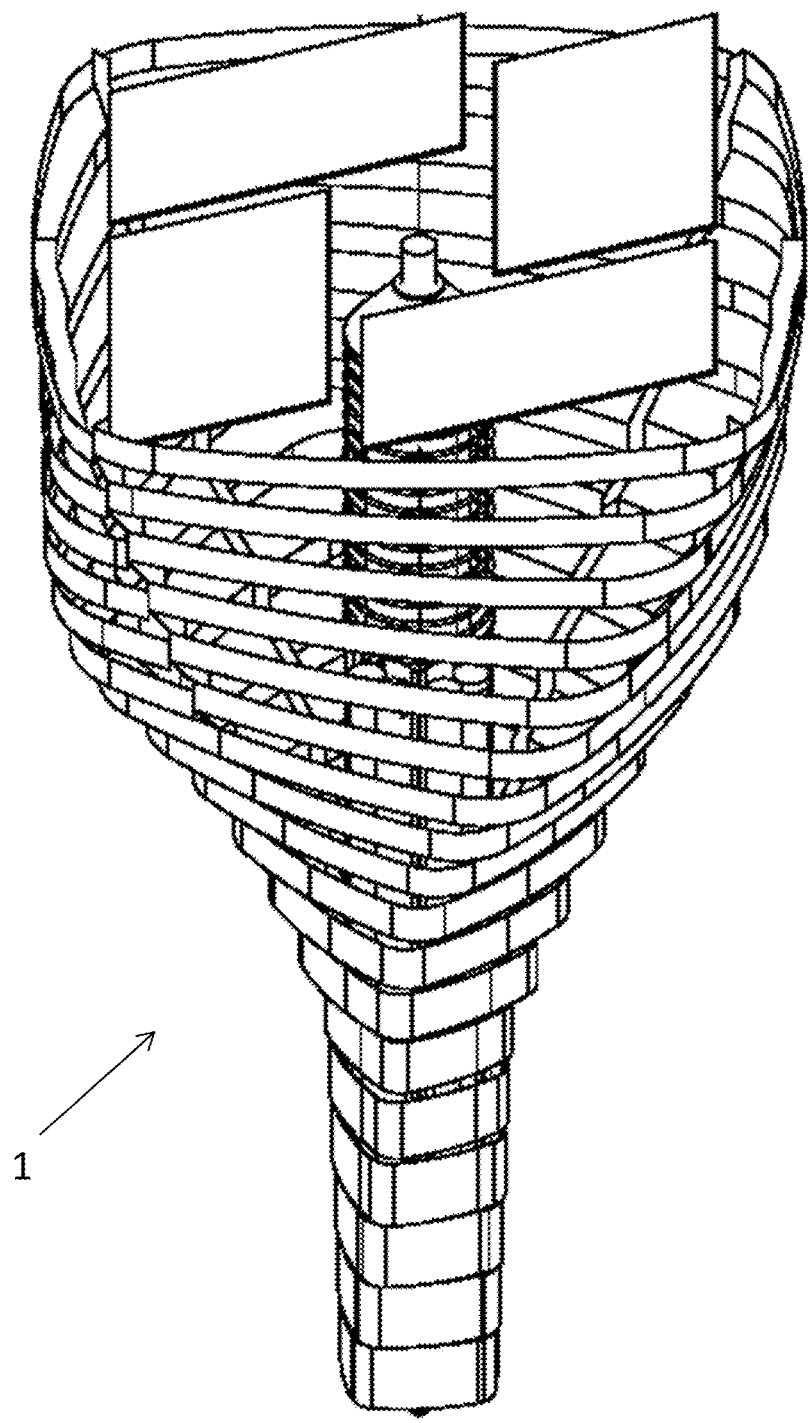
FIG. 1 shows an isometric view of the system for capturing and monitoring atmospheric polluting agents (1).
Figure 2:
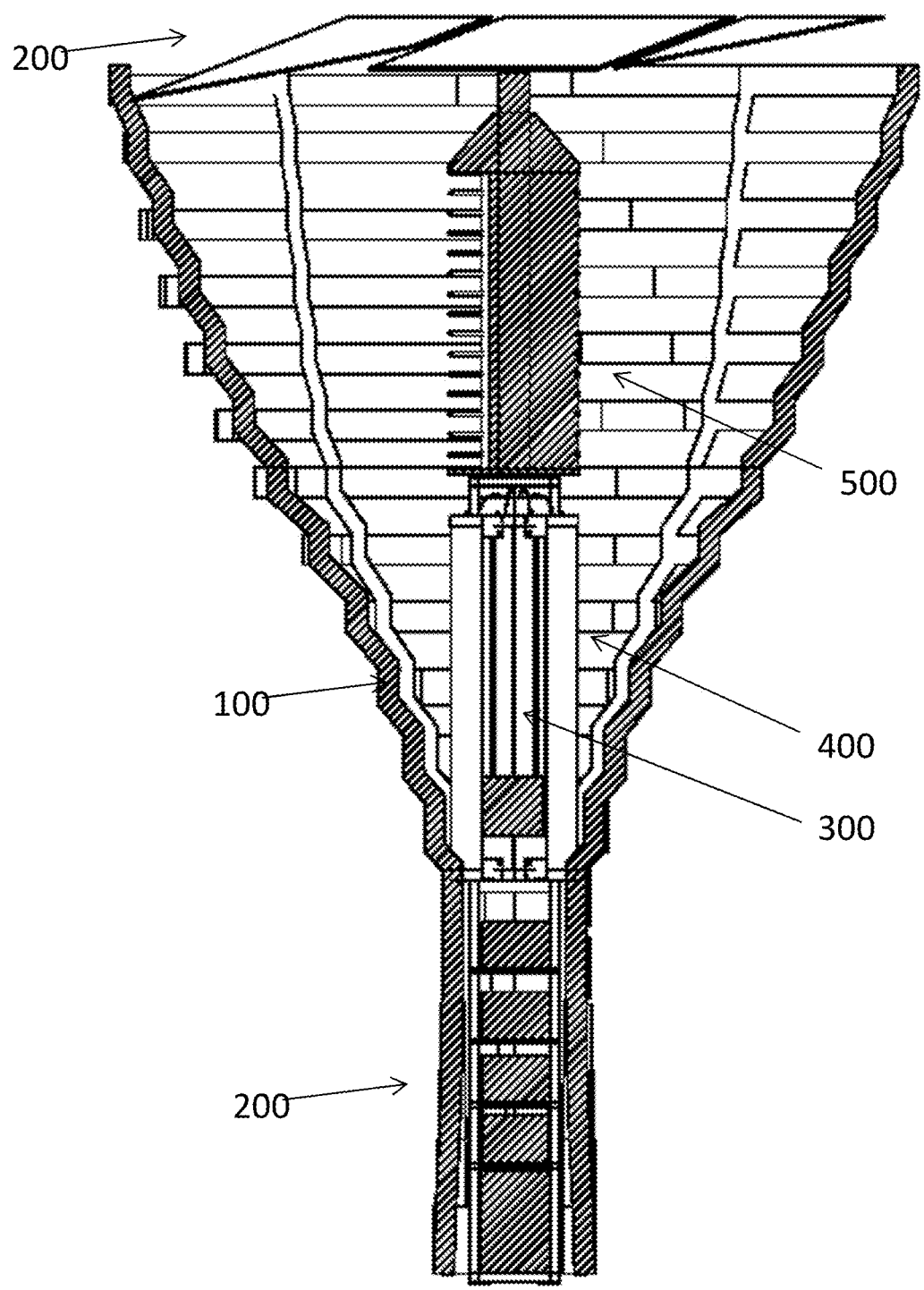
FIG. 2 shows a sectioned view of the system for capturing and monitoring atmospheric polluting agents (1).
Figure 3:
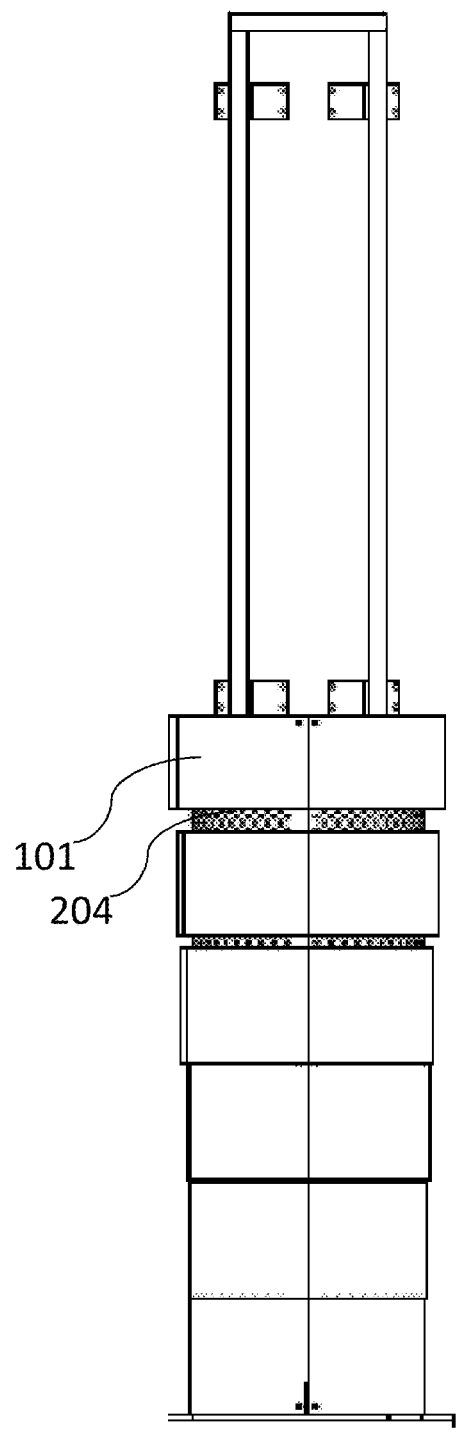
FIG. 3 shows a frontal view of the security screen (204) of the power supply module (200).
Figure 4:
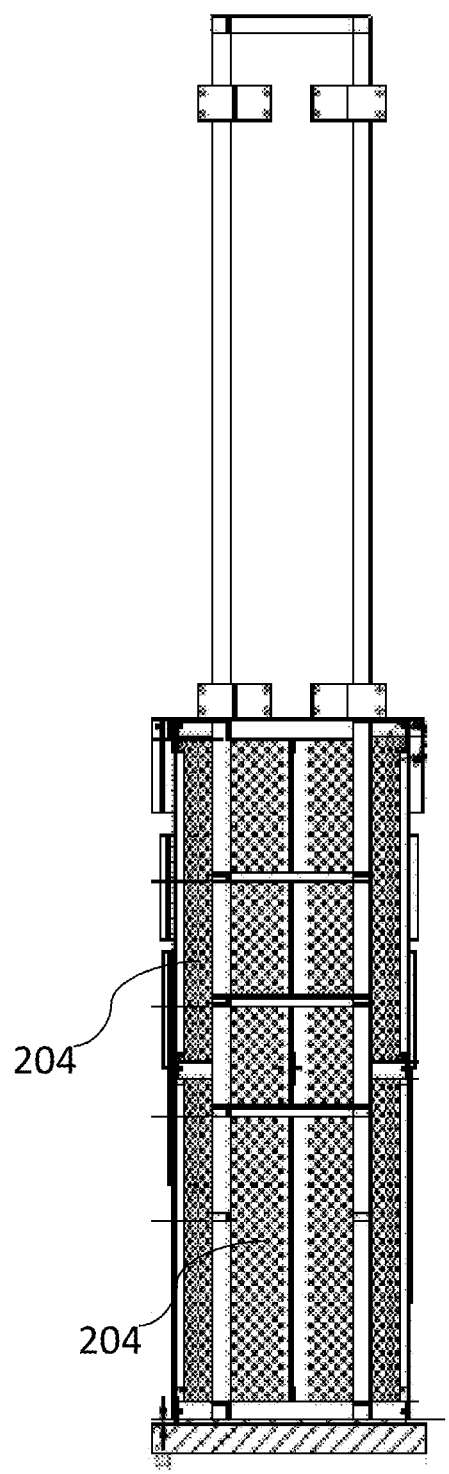
FIG. 4 shows an isometric view of the bottom part of the system for capturing and monitoring atmospheric polluting agents (1).
Figure 5:
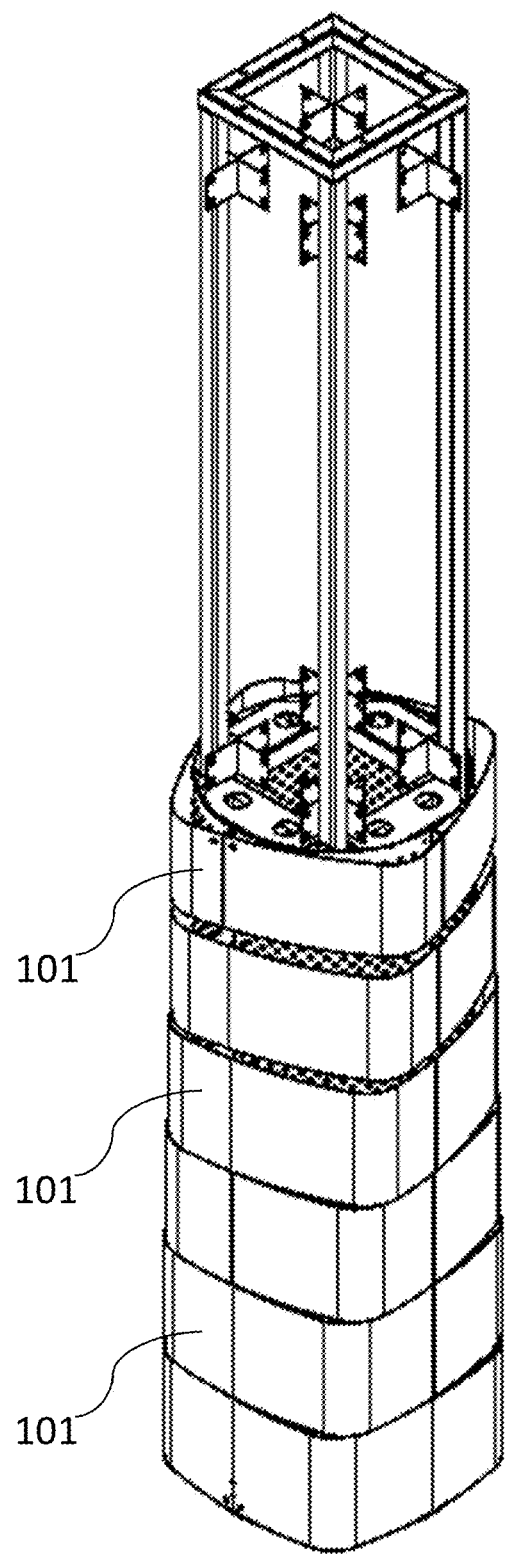
FIG. 5 shows an exploded view of the containers (302), the battery bank (202) and the particles capture unit of the present invention.
Figure 6:
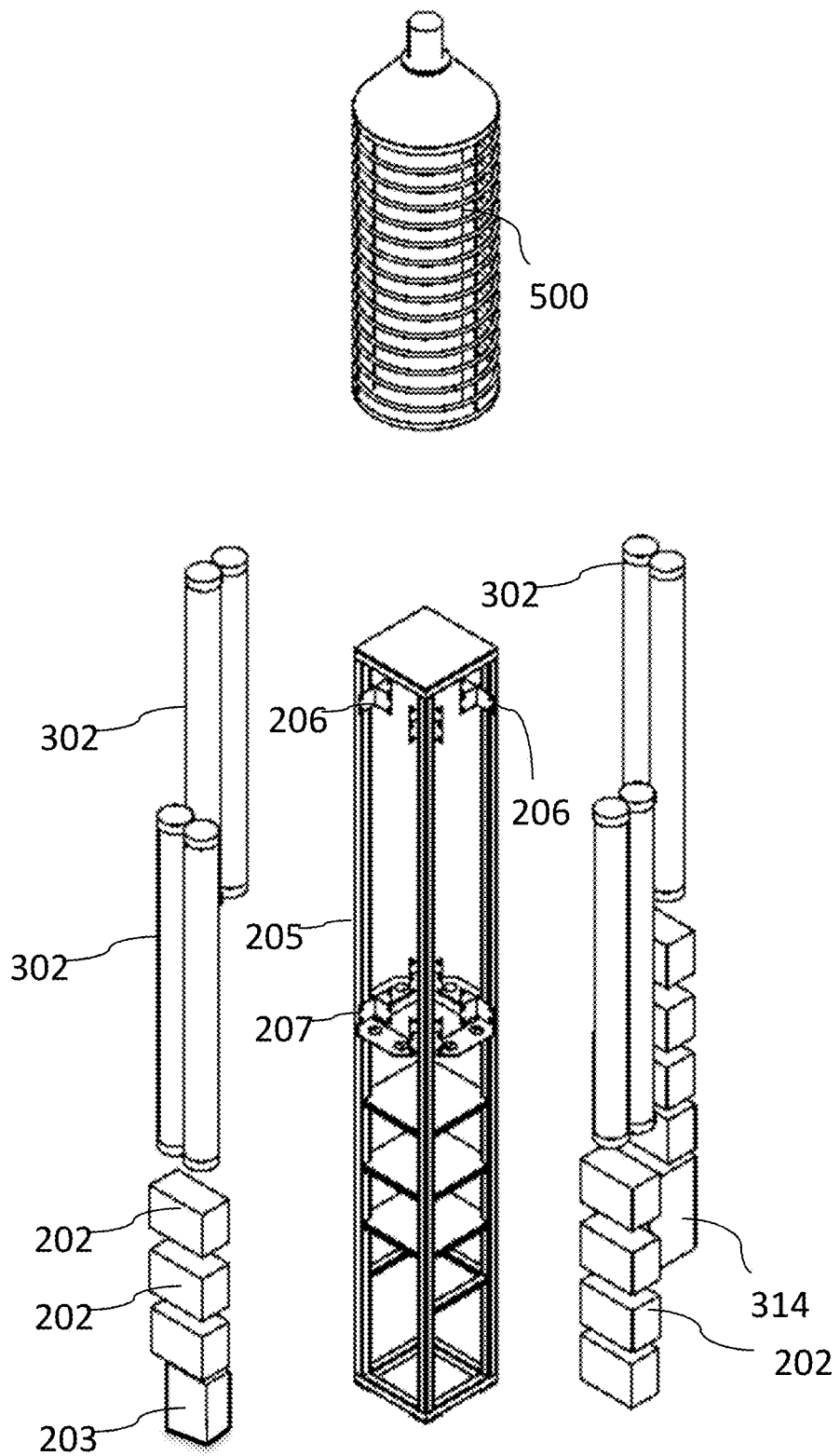
FIG. 6 shows a frontal view of the bottom part of the system for capturing and monitoring atmospheric polluting agents (1).
Figure 7:
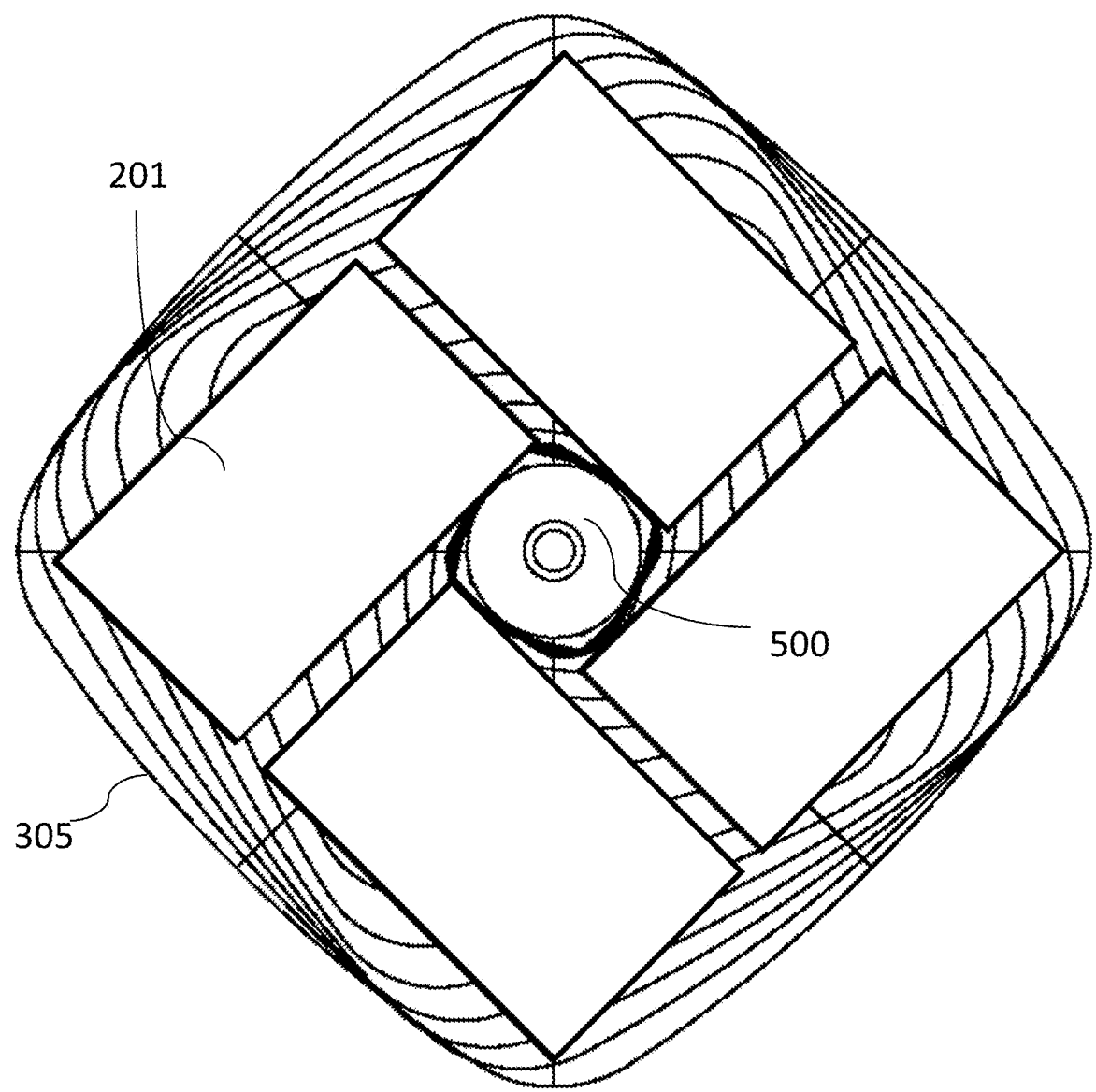
FIG. 7 shows a top view of the system for capturing and monitoring atmospheric polluting agents (1).
Figure 8:
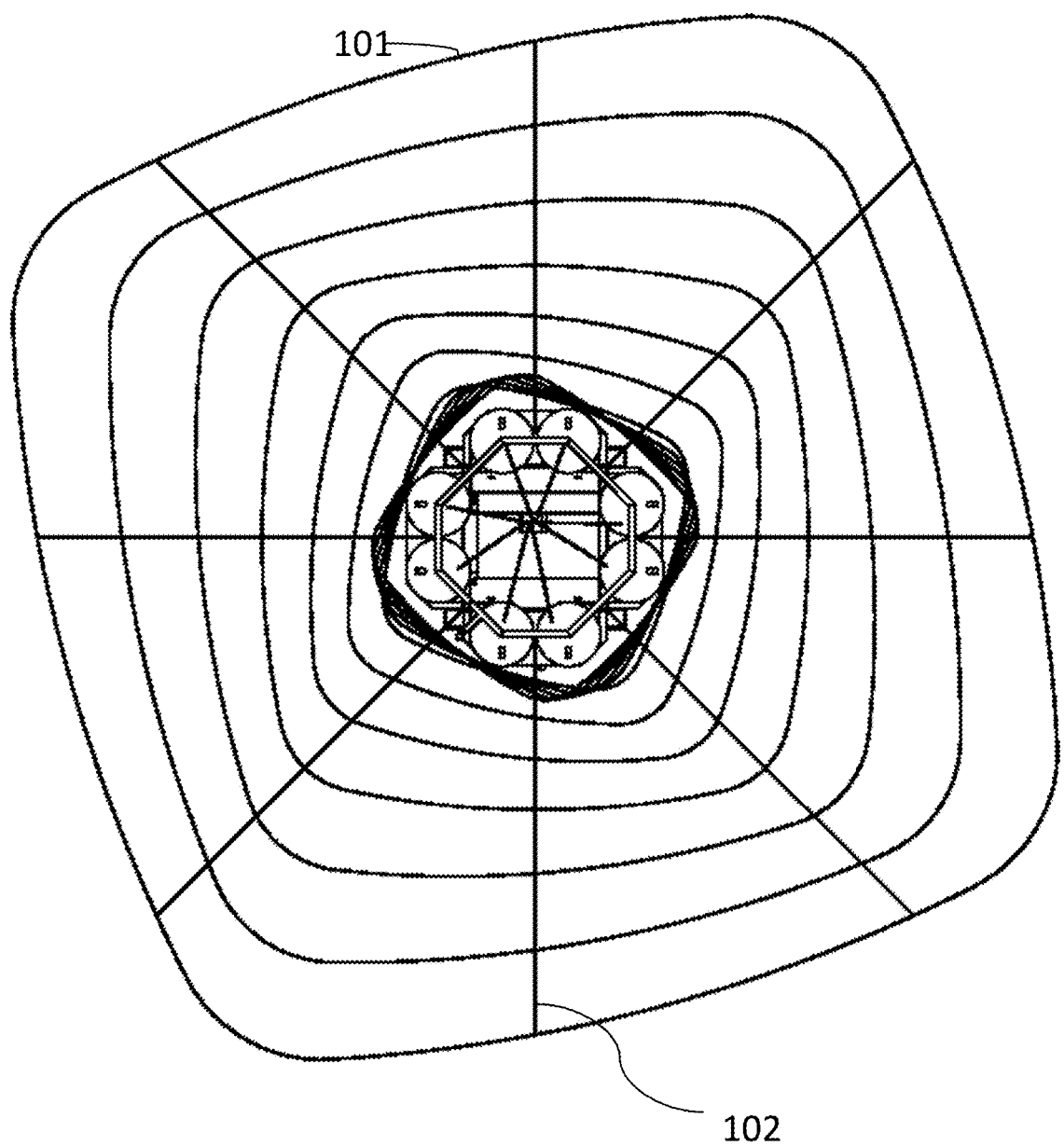
FIG. 8 shows a bottom view of the system for capturing and monitoring atmospheric polluting agents (1).
Figure 9:
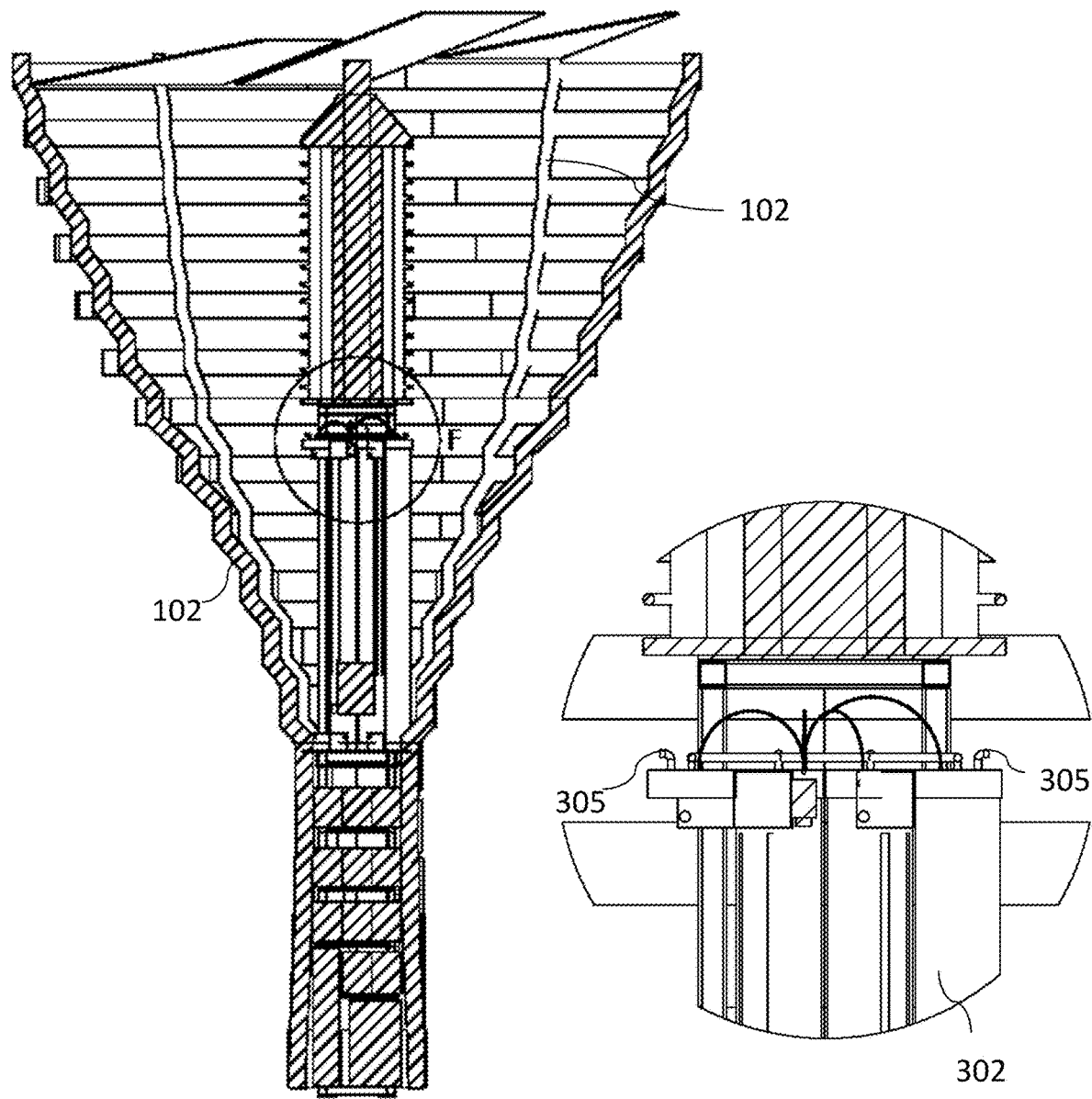
FIG. 9 shows an amplified view of the top part of the containers (302) of the bioremediation module (300).
Figure 10:
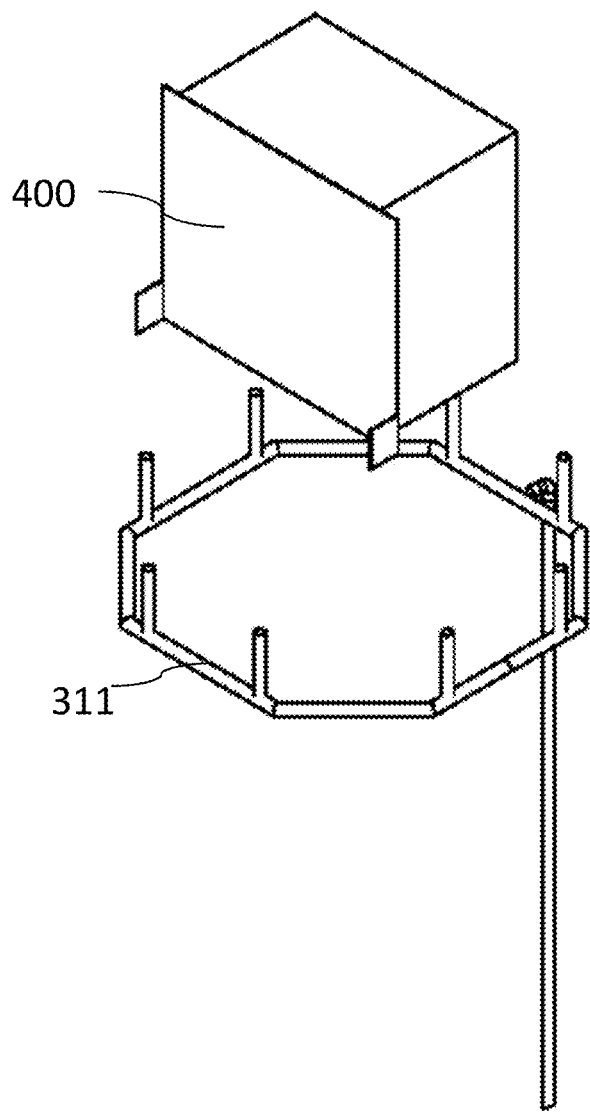
FIG. 10 shows an isometric view of the control and monitoring module (400) and of the output arrangement (311) of the bioremediation system (300).
Figure 11:
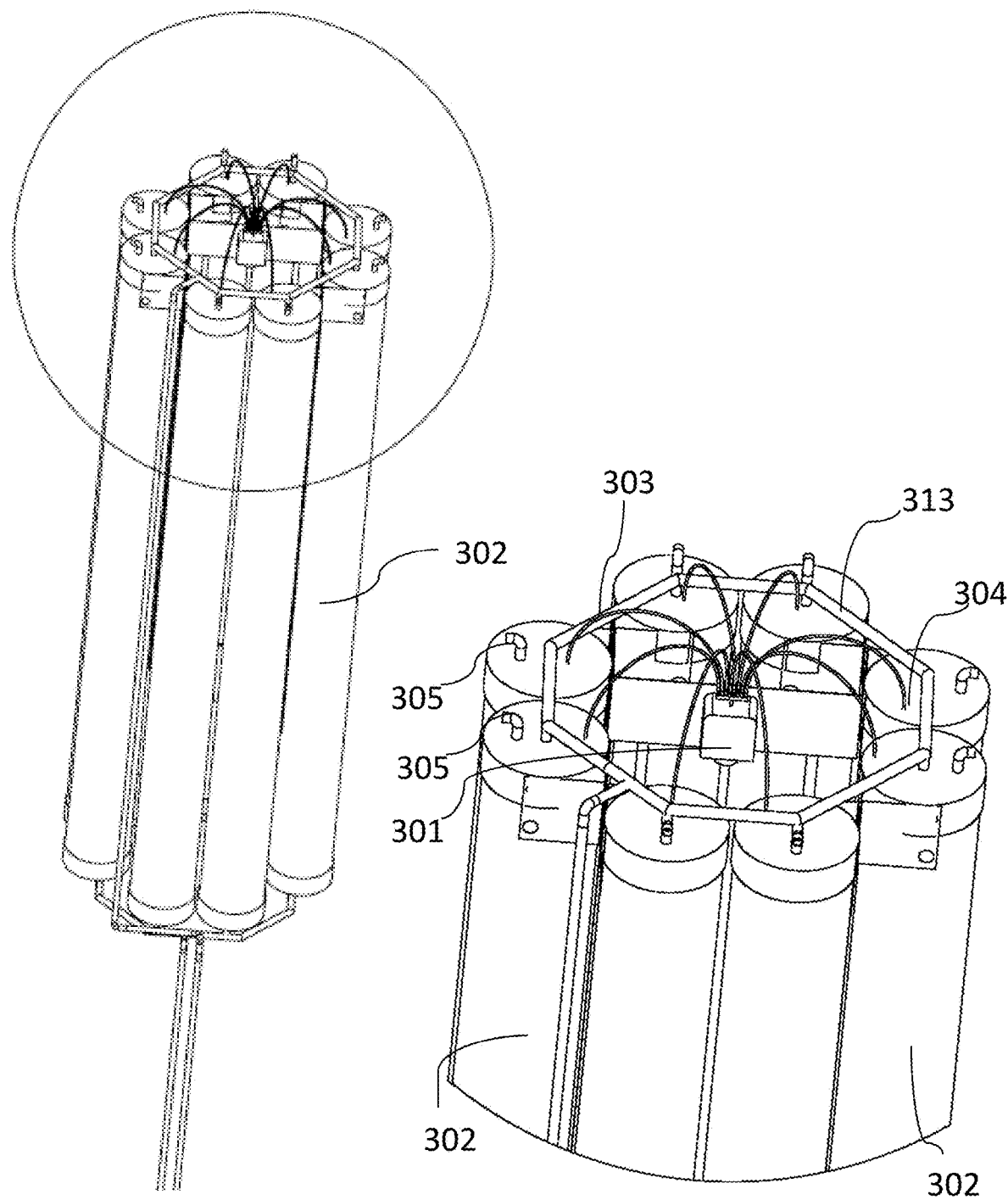
FIG. 11 shows an amplified isometric view of the bioremediation module containers (302).
Figure 12:
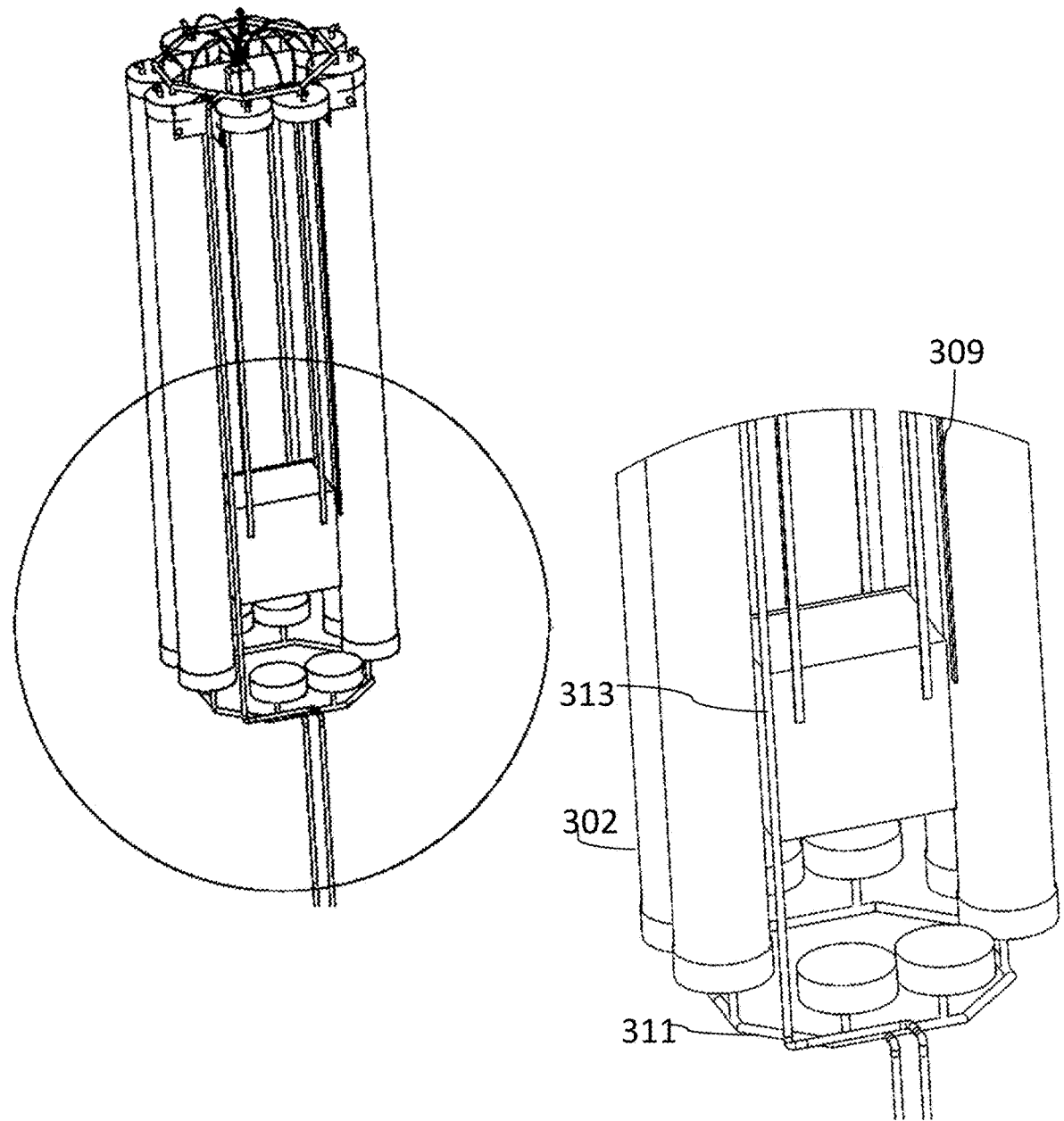
FIG. 12 shows an isometric view of the middle part of the bioremediation module containers (302).
Figure 13:
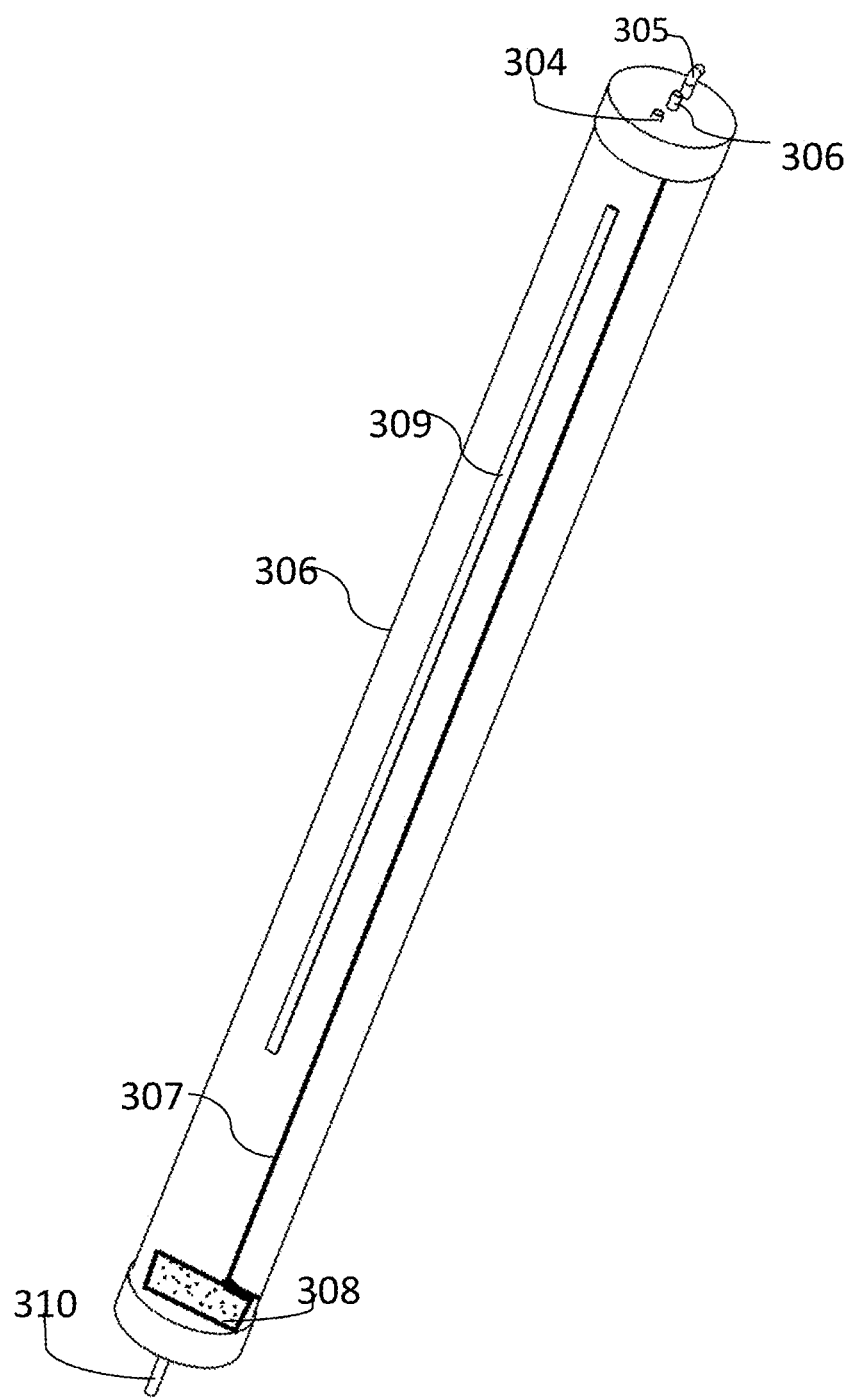
FIG. 13 shows an isometric view of one of the bioremediation module containers (302).
Figure 14:
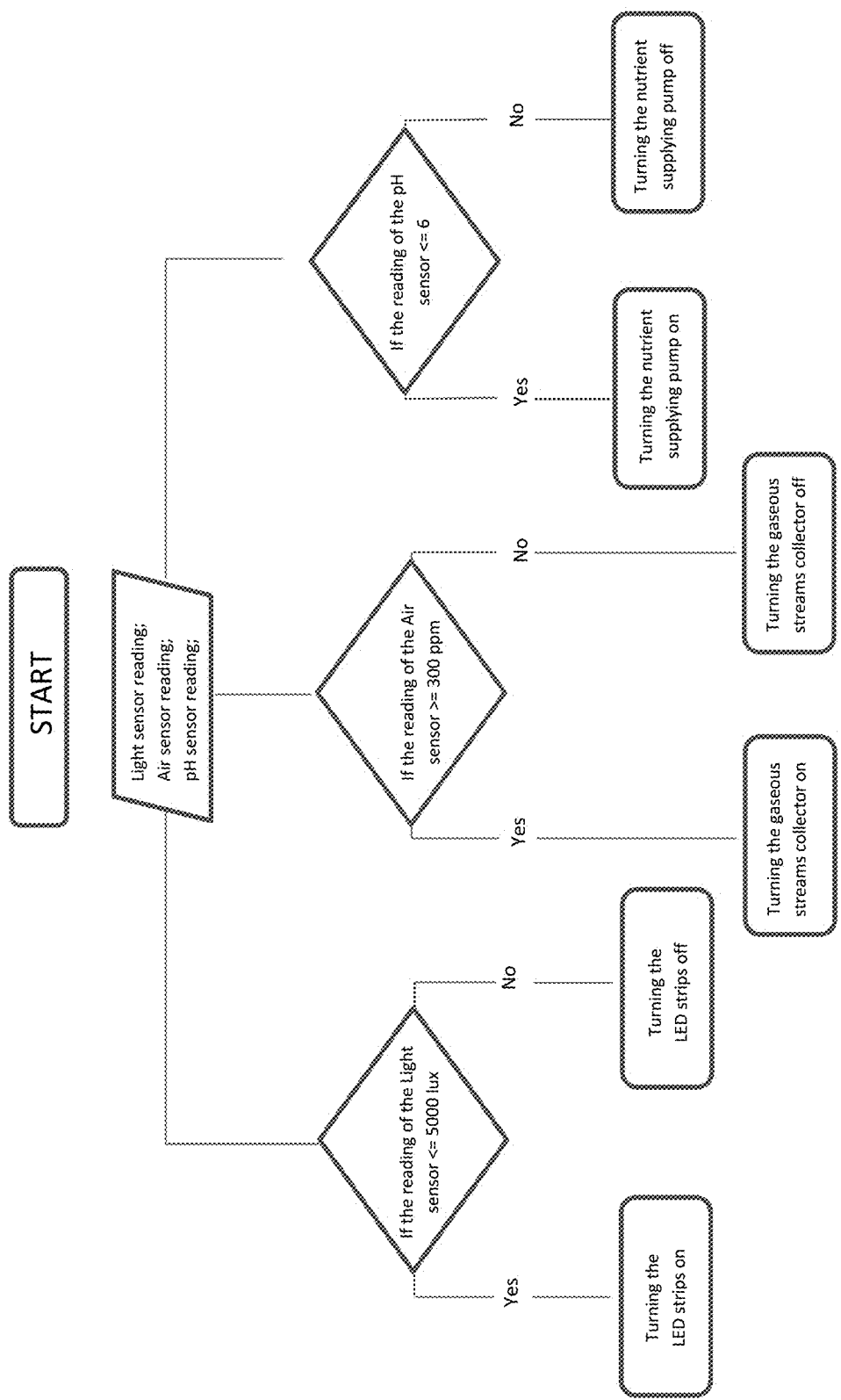
FIG. 14 shows a diagram with the steps to follow for the control and monitoring system (400).
Figure 15:
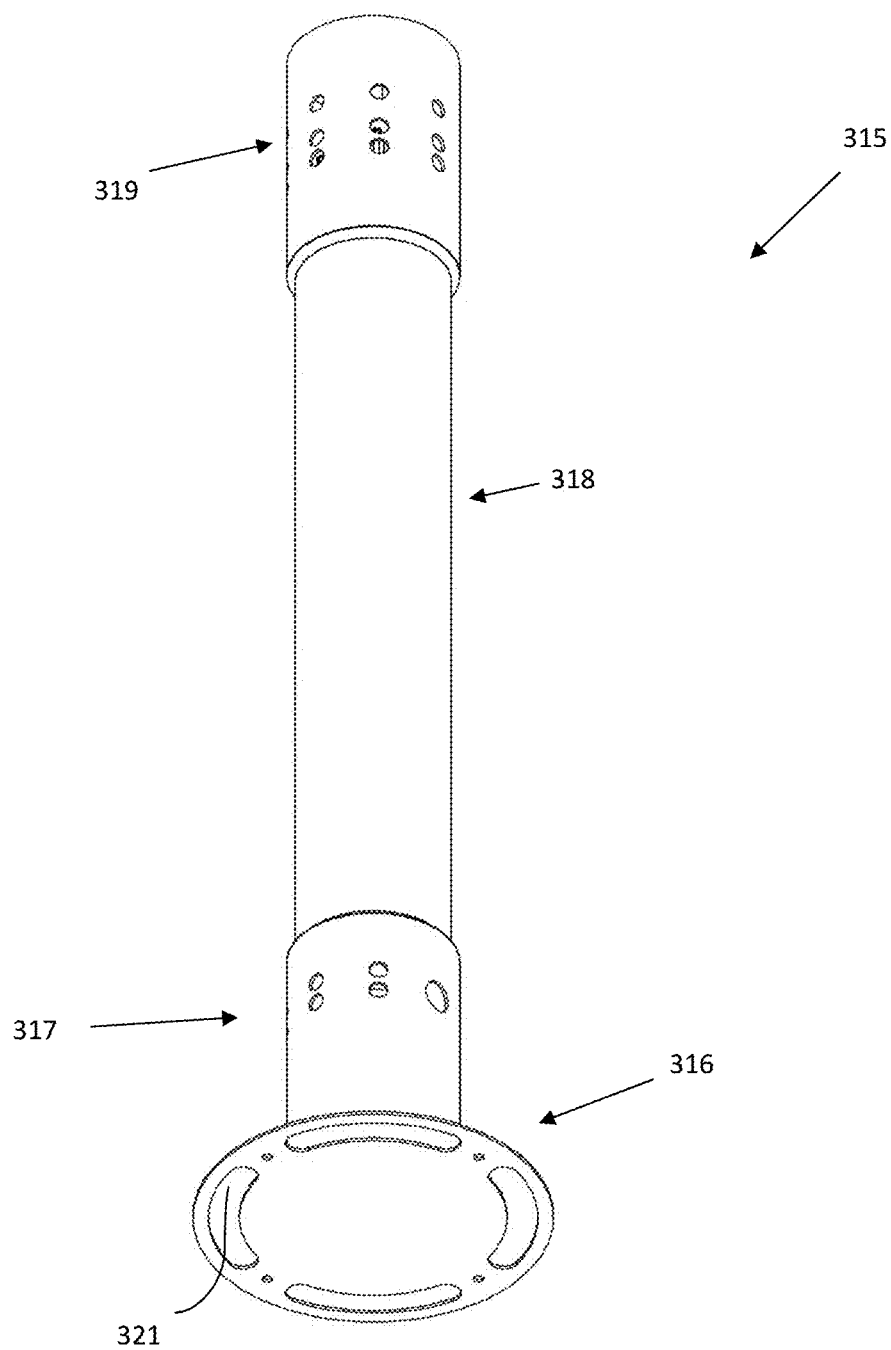
FIG. 15 shows an isometric view of the gaseous streams purifier device (10).
Figure 16:
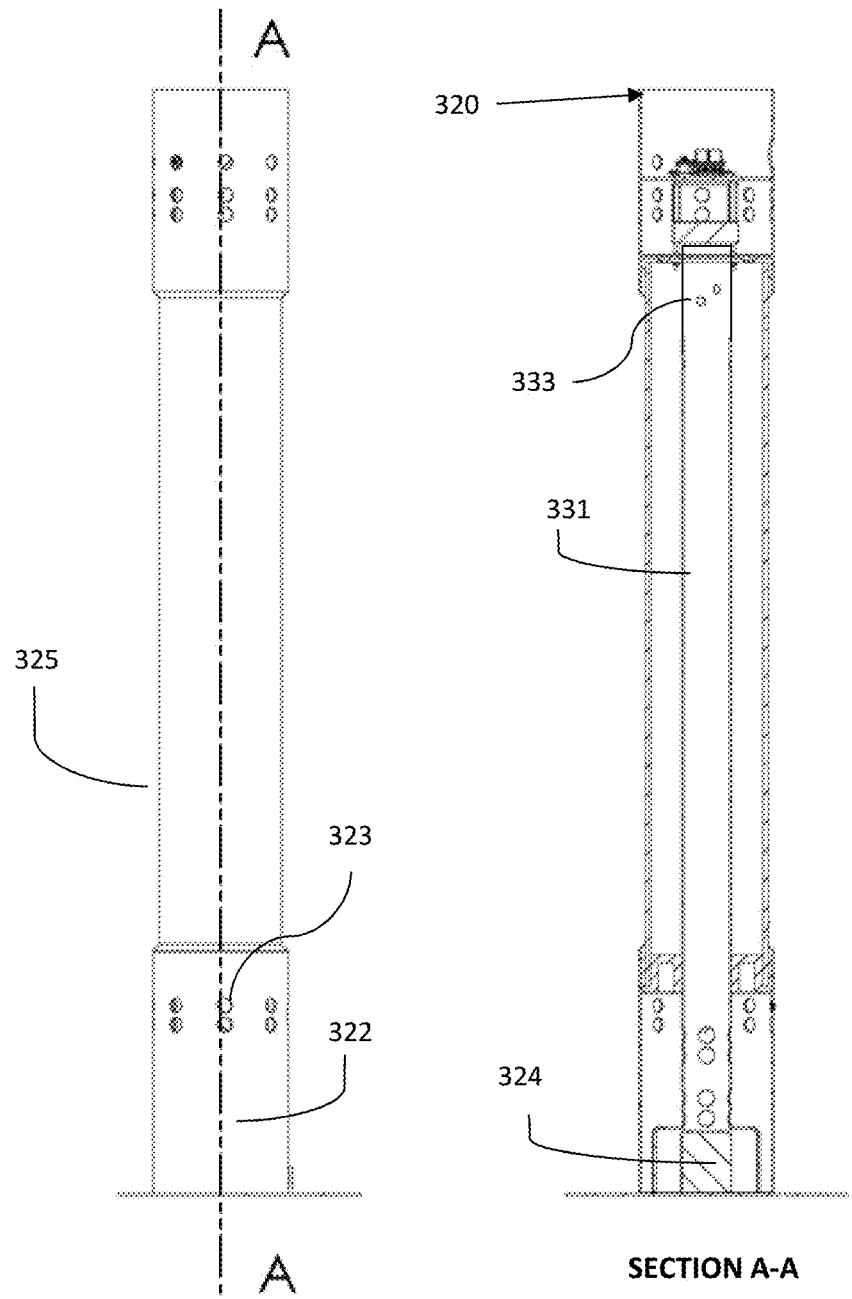
FIG. 16-A shows a side view of the gaseous streams purifier device (10).
Figure 17:
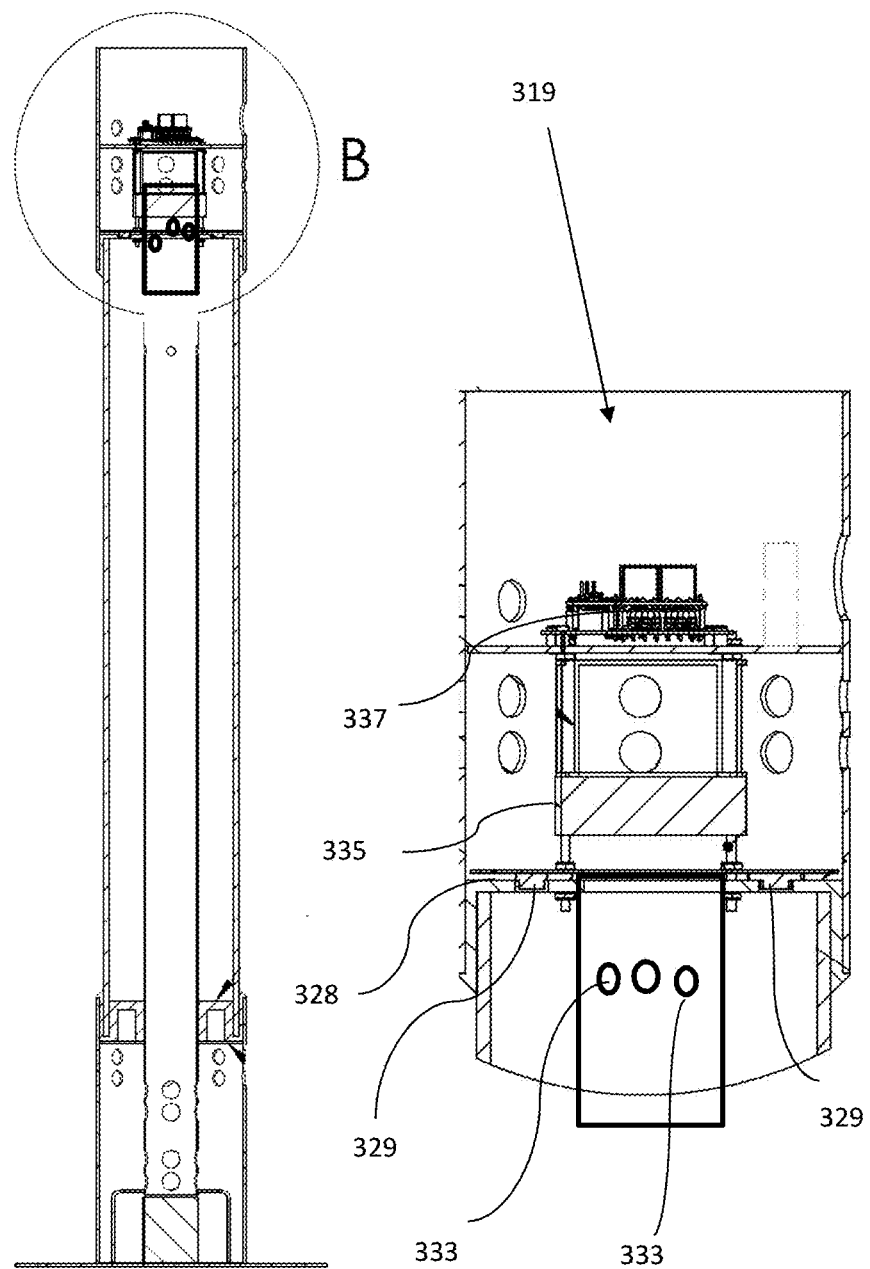
FIG. 17 shows a sectioned view of the gaseous streams purifier device with an amplification of the top part.
Figure 18:
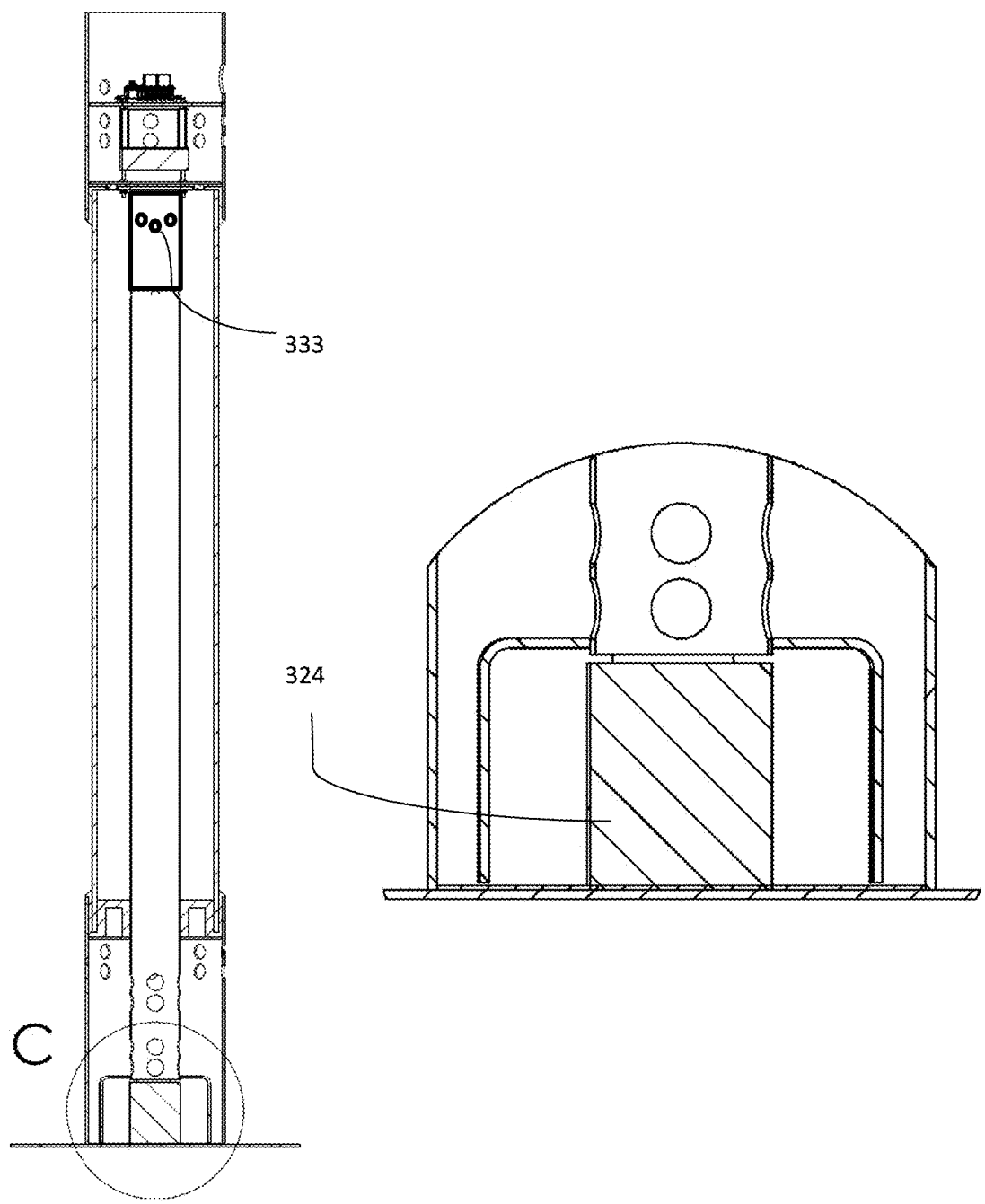
FIG. 18 shows a sectioned view of the gaseous streams purifier device with an amplification of the bottom part.
Figure 19:
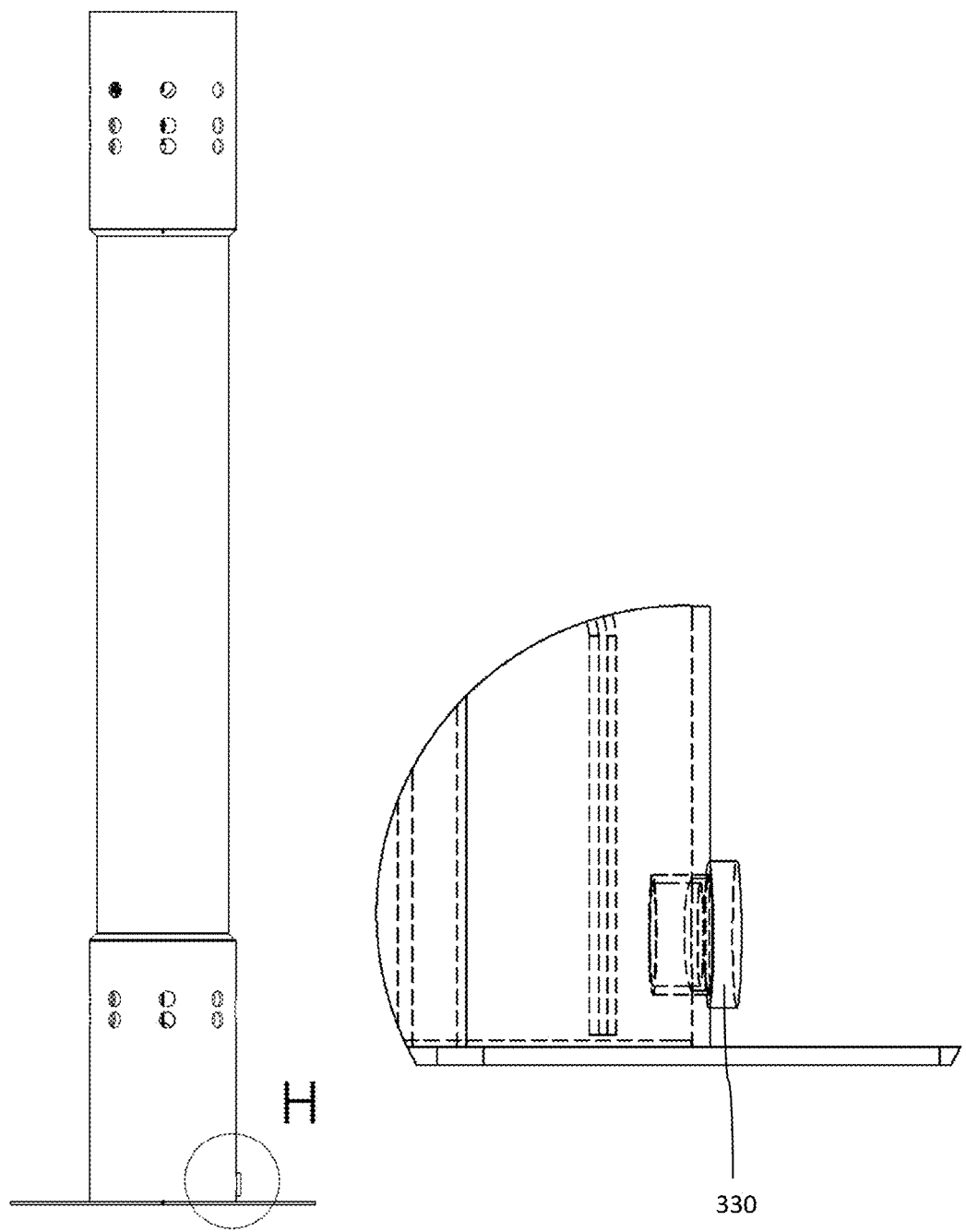
FIG. 19 shows a side view of the gaseous streams purifier device with an amplification of the plug.
Figure 20:
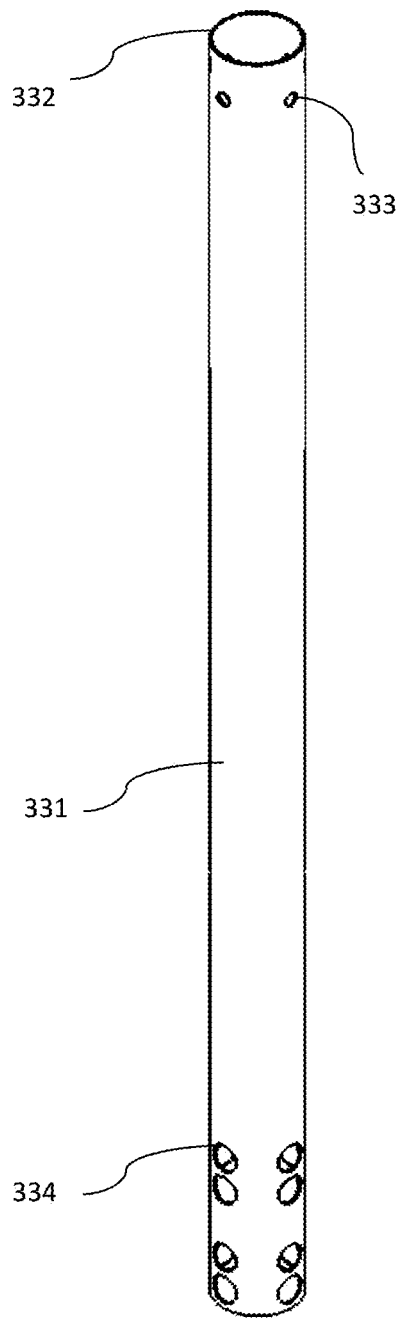
FIG. 20 shows an isometric view of the exchanger cylinder.
Figure 21:
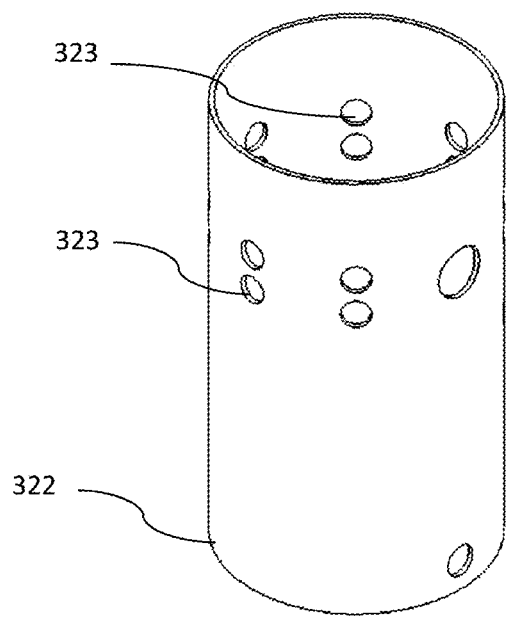
FIG. 21 shows an isometric view of the storage tank.
Figure 22:
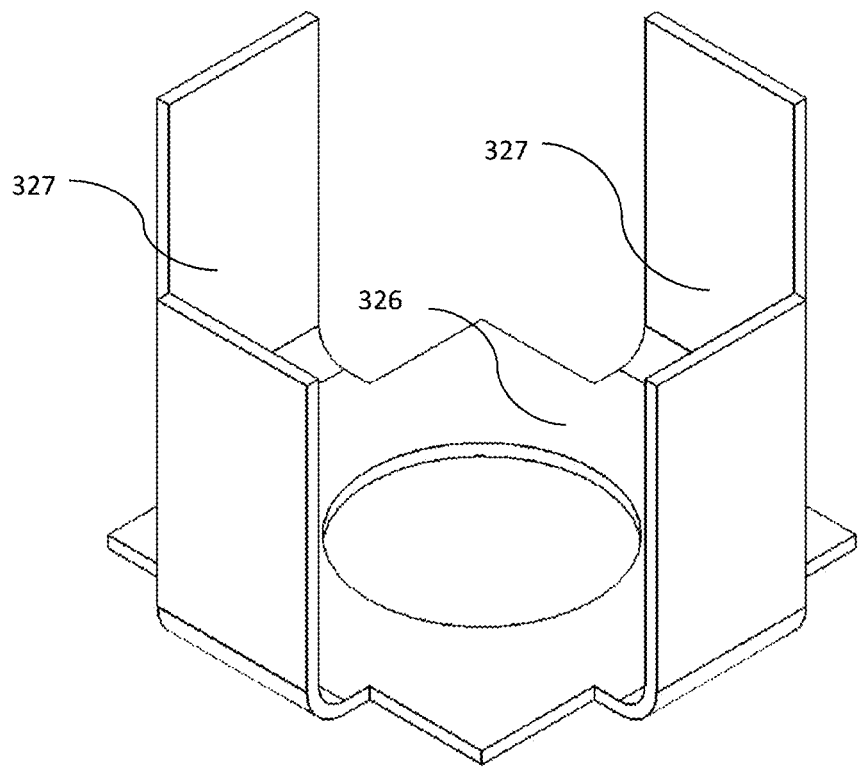
FIG. 22 shows an isometric view of the coupling element.
Figure 23:
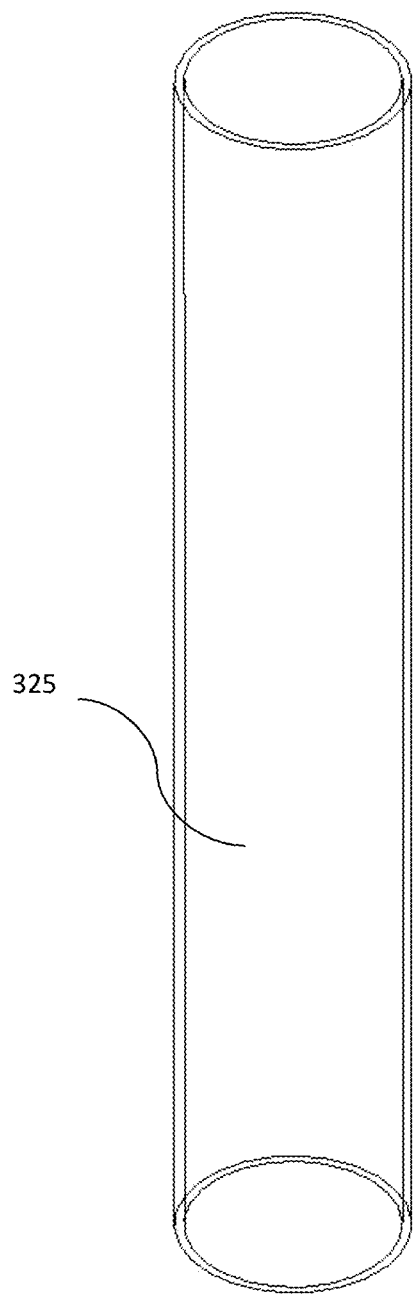
FIG. 23 shows an isometric view of the main tank.
Figure 24:
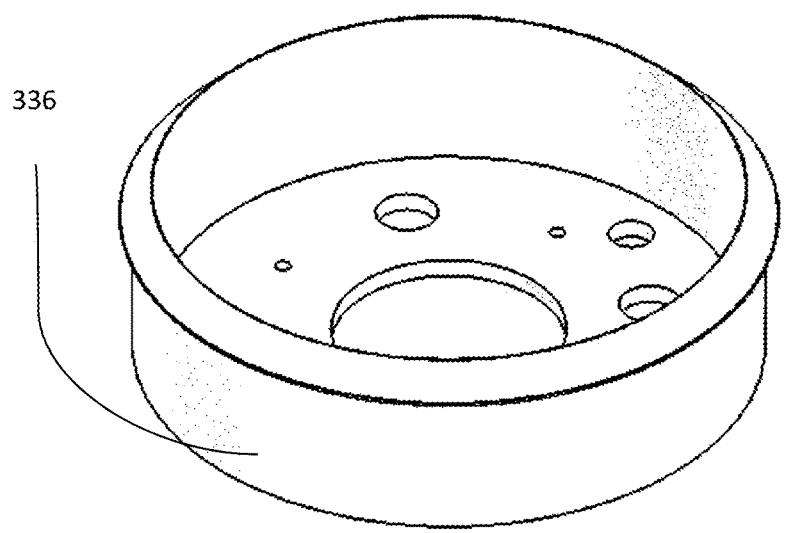
FIG. 24 shows an isometric view of the coupling cylinder.
Figure 25:
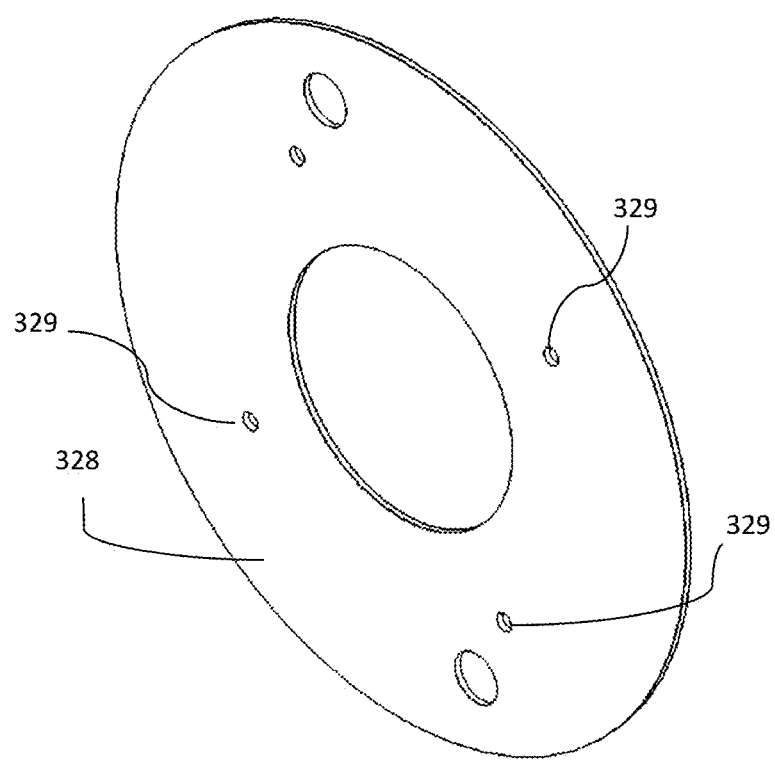
FIG. 25 shows an isometric view of the plug.
Figure 26:
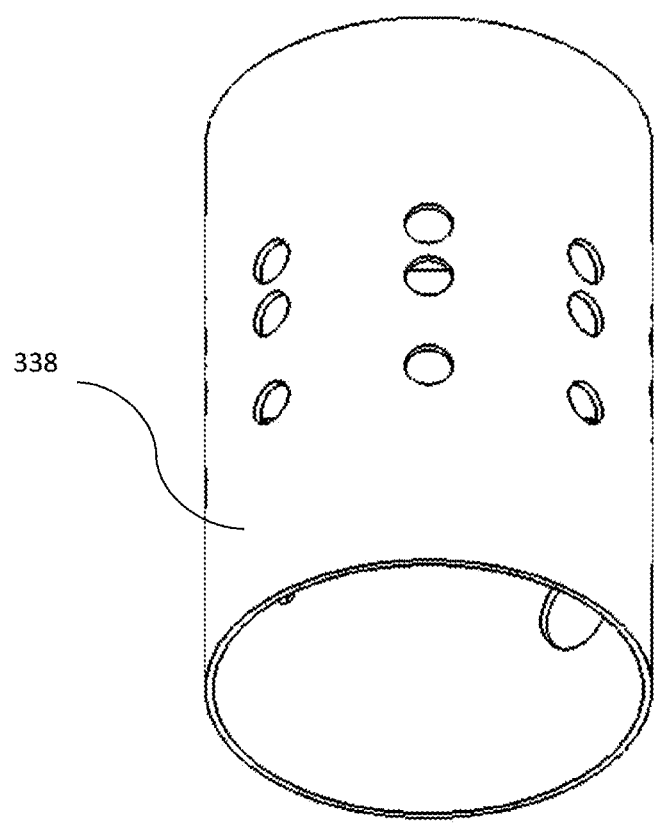
FIG. 26 shows an isometric view of the expulsion gases cylinder.

This invention refers to a system for capturing and monitoring atmospheric polluting agents (2). It was made with the purpose of providing a system for the bioremediation of gaseous polluted streams with a concentration of at least one polluting agent that could represent a risk for people's health. CO, $CO_2$, NOX and SOX are among these gases, however, we are also considering the capture of Particulate Matter 2 (PM 2) and 10 (PM 10). The capture of these particles and gases intends to avoid both, their propagation and consequences.

The system for capturing and monitoring atmospheric polluting agents (1) is generally compounded by a protection skeleton (100) that covers and protects the entire system; a power supply module (200), which provides the necessary electrical energy for the right operation and working of the system; a gas bioremediation module (300), which captures and bioremediates the polluted gaseous streams that circulate inside it; a control and monitoring module (400) which census and modifies the operation parameters. Finally, it has at least one particles capture unit (500) for capturing the solid elements that approach to the system. This has the purpose of absorbing these particles from the environment, by reducing the risks and damages they can provoke to the population.

In a preferential modality, overall, the protection skeleton (100) of the system consists in a plurality of sheets (101) characterized by a square type arrangement with rounds at their vertices:

The sheets (101) located at the bottom part of the protection skeleton (100), have the same magnitude in the diagonal distance conformed by their arrangement, preferably 75-80 cm, as well as a 3-5° rotation in respect of the axial axe they share.

The sheets (101) located from the middle to the top part of the protection skeleton; increase their diagonal distance magnitude, preferably in 30 cm intervals in ascending order.

The sheets (101) located at the middle and top parts; have a 5-10° rotation on its axial axe in respect of the axial axe of the sheet at the bottom part of each one of them.

In this way, overall, we have a helical shape body. The joint of the protection skeleton sheets is made by a plurality of joint means (102), preferably by extensions located at the rounded vertices of each of the sheets' arrangements (101).

The power supply module (200) of the present invention has an energy source, preferably a plurality of solar panels (201) located on the top part of the protection skeleton. They catch the energy contained by solar radiation, to become then it into electric power. The panels are connected to a battery bank (202), which is preferably at the bottom part of the system for capturing and monitoring atmospheric polluting agents (1). The battery bank has the function of storing the charge coming from the solar panels (201), to be then connected to a power inverter (203), which converts the direct current electric power coming from the panels (201) into alternating current electric power. The latter supplies the gaseous streams collector (301), the monitoring system (400), so as to a plurality of Light-Emitting Diodes strips (309) belonging to the gases bioremediation system (300).

Furthermore, the power supply module (200) has a security screen (2014), which has the purpose of avoiding the introduction of external objects able to provoke, either some damage to the system or an accident to any individual who try an interaction.

A particle capture unit is located at the top part of a frame (205) that is in the axial axe of the protection skeleton. It is worth mentioning that there is a plurality of bioreactors (302) joined by mean of a plurality of coupling brackets (206) in a zone next to the superior part of the frame. Moreover, the frame (205) accounts with a medium base (206) located at its middle part that works as a support for the bottom part of the bioreactors that overlap on it. Finally, there is a plurality of bases (207) in which some of the batteries of the battery bank are stored (202) at the bottom part of the mentioned frame (205).

In another regarded modality, the energy source is supplied by a connection to the distribution lines of the local (company) electric power supplier. Another modality considers the possibility of supplying energy with an electrical generator, which transforms magnetic flow into electricity by mean of electromagnetic induction in order to generate a direct current. The latter can be achieved by mean of bicycles adapted to such end.

The gases bioremediation module (300) has the function of attracting the polluted gases from the environment in order to dissolve them into an aqueous medium. The module has at least one bioreactor (302) with a storing capacity of at least 10 liters (preferably 25) and it is preferably cylindrical. The bioreactor has an air input (304) with a plug. Air is introduced by mean of a duct (303) that transports the gaseous polluted streams coming from the environment that are introduced by the gaseous streams collector (301). The latter is located in a zone next to the middle part of the system (1).

The gaseous streams collector (301) introduces the contaminated air from the environment, with a flow between 10 and 80 liters per minute, preferably 60 liters per minute. The duct (303) connects to a conductor (307) that reaches the bottom of the bioreactor (302). Moreover, there is a diffuser coupled with its opposite end (308), which has the purpose of expanding the polluted gaseous streams transported by the conductor (303) from the bottom of the bioreactor (302).

The bioreactor's plug (302) has an air output (305) destined to expel the treated and purified air. It also has a filling entry orifice (306), which serves to introduce the aqueous medium with the photosynthesizer microorganisms. The filling entry orifice (306) can also be used for managing severable solutions, such as nutrients, disinfectant agents, among others.

In an advantageous modality, the gases bioremediation module (300) has a set of eight bioreactors (302), which are preferably disposed in a circular arrangement. The filling of the bioreactors' arrangement (302) is made by mean of a hydraulic pump (not shown) which lifts the solution from the storage (314) located at the bottom part of the system (1). The solution is introduced by mean of an arrangement of conductors (313) that connects with the filling entry orifice (306). The conductor's arrangement (313) also has a valve (not shown) at the air input of each bioreactor (302), which is in communication with the control and monitoring module (400) in order to supply the adequate solution amount.

In this modality, the plurality of circumferentially disposed bioreactors (302) process an air amount between 40 and 80 litters by minute, preferably 60 litters per minute. The stream gaseous collector (301) is programmed to work in 8 hours intervals. After this time, it turns off to begin with the photosynthesis process.

Bioremediation happens in the bioreactor (302). Bioremediation, is the process used by microorganisms, fungi, plants (and enzymes derived from them) in order to return a contaminated environment to its natural condition. Due to the bioreactor works with an aqueous solution inside it, preferably microalgae and/or cyanobacteria, it is necessary to keep them alive during its operation. One of the most important elements for the growth of the photosynthesizer microorganisms, are the nutrients (in solution) rich in carbon and nitrogen. In the case of this invention, the nutrient sources are $CO_2$, greenhouse gases, Nitrogen Oxide and atmospheric pollutants that are introduced into the system by mean of the gaseous streams collector (301)

In a preferential modality, the desirable solution is a nutritive one, and it is stored in the storage (314). The nutritive solution is preferably selected from a sterilized formulation with a 1:2 p/v vermicomposting diluted in water relation.

Nevertheless, it must be understood that there are several available nutritive solutions, but the requirements are different for each microalgae/cyanobacteria species. Furthermore, the species has to be considered in order to define the composition of the cultivation medium. For instance, while some species such as *Tetraselmis* sp., *Chlamydomonas* sp., and *Nannochloris* sp need no more than 15% of $CO_2$ in order to grow, others, such as *Scenedesmus* sp. and *Cyanidium caldarium* tolerate $CO_2$ concentrations from 80% up to 100% respectively. Preferentially, the bioreactors of the present invention keep any of the next microalgae and/or cyanobacteria inside them: *Synechocystis, Spirulina, Dunaliella, Dunaliella, Chlorella, Tetraselmis, Chlamydomonas, Nannochloris, Scenedesmus, Cyanidium, Anabaena, Nostoc*, mixtures of them, either in monoculture or polyculture, or any other of commercial interest.

In another modality, the bioreactors (302) are able to contain microalgae and/or cyanobacteria native from the place where the system for capturing and monitoring atmospheric polluting agents (1) is installed. The latter has the purpose of optimizing the control resources of the growth parameters. The native species are selected and isolated due to their efficient capacity to hold high $CO_2$ concentrations (or other polluting agents), and because they are able to tolerate the weather conditions of the place.

The selection of species to cultivate can depend on the wanted use for the resulting biomass. That is to say, advantageously, that the biomass can be used for cosmetic, feeding, agronomic, or any other known end.

Moreover, the bioreactor (302) has a pH sensor (not shown), which keeps communication with the control and monitoring module (400). It identifies when the pH parameter is outside the programmed range, and sends a signal for a dispenser (not shown) to manage a base (or alkaline) solution which allows to newly stabilize the parameter. A draining drill hole (310) advantageously connects to an output arrangement (311). This connection gathers the outputs of all the draining drill holes of the containers' arrangement (302), which has a draining valve (not shown) that allows to void the containers' content at the same time. The latter facilitates the maintenance of the gases bioremediation module (300).

The microalgae/cyanobacteria production increases proportionally along with temperature up to achieving an optimum temperature for each species. If temperature is higher than needed, breathing increases and photorespiration reduces global productivity. Therefore, the adequate temperature could variate between different species. Thus, in a preferential modality, the system (1) is able to have a mean for controlling and monitoring temperature, such as a water sprinkler or a solar thermal collector. Moreover, the bioreactor (302) is advantageously made of a transparent material (preferably acrylic of 6 inches thick) that allows light. This favors temperature control.

There is at least one strip with a plurality of Light-Emitting Diodes (LED, 309) at the bioreactors periphery (302), preferably able to provide around 3 thousand white light lumens in periods between 8 and 12 hours in order to give light to the solution from inside the bioreactors (302). Light intensity is one the main parameters for the cultivation. This is because, if limitation of nutrients happens, photosynthesis increases along with light intensity up to reach the maximum growth rate particular of each species at the light saturation point. Overcoming this point provokes photoinhibition, by causing harmful results to the cell, and even the death. This leads the cultivation to loss photosynthetic efficiency and productivity. Finally, the power supply for the Light-Emitting Diodes stripes (309) comes from the power inverter output (203) of the power supply module (200).

The monitoring and control module (400) has a power source connected to the power inverter output (203). Furthermore, a programmable logic controller and a set of relays are connected to the air quality sensors. The monitoring system controls the hydraulic pump and the LED strips (309). Moreover, the module has a plurality of air quality sensors in order to determine the operation conditions of the system. The system for the capture and monitoring of atmospheric polluting agents (1) works under the next logical programming.

The logical programming that determines the functionality of the system has a reactive nature according to the monitored data by mean of the light intensity sensors within the LED strips (309), air quality and pH sensors.

The LED strips (309) for the light supply energy activate in respect of the real time monitored irradiation, by mean of brightness sensors, and under certain quantity of lumens on time.

The gaseous streams collector (301) activates according to the gases and particles concentrations monitored by mean of the air quality sensors.

The hydraulic pump (for nutrients supply) activates according to the features and behavior of the pH of the gases biofiltration system.

The particles capture unit (500) is located at the top part of the system (1). It not only inverts the polarity of the particles around it, but also attracts them. The power supply of the unit comes from the power inverter of the power supply module (200). The particles capture unit (500) is preferably the one widely depicted within the international request WO 2013/051931 (A1), which consists in a supporting structure, an electrode with an emitting conductor and a guide surface.

The guide surface is separated (and it is parallel) to a wire in a first perpendicular direction. The guide surface has an electrostatic charge that is different in respect of the wire in order to provide electrostatic force. The supporting structure consists in a bar that is separated from, and parallel to the wire in a second perpendicular direction. The second direction has a component opposite to the first direction, and a component that is perpendicular to the first direction. The bar has an electrostatic charge different in respect of the wire in order to boost the particles flow, in a way in which it follows a loop path around the wire and the bar.

Advantages

According to the aforementioned, the advantages of the present invention could not be overlooked by a technician of the field. Among them, it is worth mentioning the bioreactors (302) together with the conductor's arrangement (313) and the output arrangement (311) that allows the bioreactors (302) to work independently, either for maintenance, avoiding a massive contamination, inoculating monocultures, polycultures and native cultivations within the same system. Moreover, the latter is monitored and controlled in real time in order to have an autonomous decision making and guaranteeing the optimum working of the system (1).

Furthermore, the system (1) offers an advantage to comprehend the working of bioreactors in outdoor spaces and favorable working conditions, independently of seasonal variation. It is worth highlighting that it provides a facility to harvest biomass, to do the maintenance of the cultivation without contamination, and for controlling and monitoring the cultivation conditions. The latter has a direct impact on the wanted conditions by enabling the reduction of operation costs.

Apparat from the already discussed technical advantages, which are mainly focused on the bioremediation of polluted gaseous streams and the capture of polluting particles, the ornamental design of this invention (conferred by its completely new protection skeleton, 100), allows the system to be installed in places such as: roads, parks, public spaces, residential complexes, malls, universities and airports, among others. That is why, in another modality, we regard the inclusion of a wireless access point for users to be able to connect their devices to internet, so as outlets, video surveillance cameras, panic buttons and traffic flow sensors at the protection skeleton's periphery, whose functions and features are well known within the state of the technique.

In a preferential version, the present invention regards a bioreactor arrangement. Here after, the bioreactor will be called "polluted streams purifier bioreactor" (315). It was designed with the purpose of attracting polluting substances from an environmental air stream, making it pass through inside it, which is where the biological exchanger with microalgae (cyanobacteria or any other biological medium) is. In this way, it advantageously provides the possibility of restoring the aforementioned current in order to be returned to the environment. This has the purpose of purifying air in any space where required. At least one polluted streams purifier bioreactor (315) can be installed in the system for capturing and monitoring atmospheric pollutant agents (1) as described before, however, this modality also considers it to be used independently.

The polluted streams purifier bioreactor (315) is compounded by a series of modules that work together for the purification of a gaseous stream; an energy supply module (not shown), which provides electrical energy to the components of the polluted streams purifier bioreactor (315); a base module (316), confined to be the structure that provides support and stability (located at the bottom part); a liquid containment module (317), which intends to store the medium (nutritive solution) that requires a variety of microalgae/cyanobacteria for an optimum growth; a streams exchange module (318), destined to provide the elements that allow a stream (polluted at a certain level) to be displaced to the interior of the polluted streams purifier bioreactor (315), by allowing to have an exchange of elements such as Carbon Monoxide (CO), Nitrogen Oxides (NO, $NO_2$, NOx), Sulfur Dioxide ($SO_2$), among others; a module for the capture of gaseous streams (319), which is the place where the contaminated streams are introduced from the exterior in order to be treated. Finally, it also has a control module (320) compounded by a Printed Circuit Board (PCB) to control several functions of the polluted streams purifier bioreactor (315)

While in one modality, the power supply module of the polluted streams purifier bioreactor (315) is an electric installation with conventional conductors supplied by the electric network, in another one, it disposes of solar panels to provide power to its elements.

The base module (316) is disposed at the bottom part of the system. It is principally compounded by a main base, which preferentially has a circular shape with a plurality of slots and bottomless drill holes (321) in zones next to its periphery. By mean of the latter, and of a plurality of securing means (such as screws and bolts), the system is embedded on a substratum. In this way, the polluted streams purifier bioreactor (315) is permanently fixed on the places where is installed. The storage tank (322), which belongs to the liquid containment module (317), is erected at the middle part of the aforementioned base.

The liquid containment module (317) of the polluted streams purifier bioreactor (315) is mainly compounded by a storage tank (322). The latter has a plurality of bottomless drill holes (323) on its periphery, which are disposed to be the mean by which a polluted stream is introduced into the polluted streams purifier bioreactor (315). The storage tank (322) contains a nutritive solution, so as a hydraulic pump (324) to send the solution towards the top part of the main tank (325).

The main tank (325), which also belongs to the liquid containment module (317), has preferably a cylinder shape, and it is attached to the storage tank (322) by mean of a coupling element (326). The latter has a square base, a bottomless drill hole on its central part, so as a plurality of supports (327) which erect ascending in respect of the base. The supports (327) have the purpose of providing stability and support to the main tank from inside the polluted streams purifier bioreactor (315). Both, the main (325) and the storage tanks (322) contain the same nutritive solution. The main tank (325) has a circular plug on its top part (328). The plug has a plurality of bottomless drill holes (329) on its surface, and a main drill hole of larger dimensions on its central part. Is at the top part of this plug (328) where the nutritive solution is sent by the hydraulic pump (324), it falls, and by mean of the drill holes (329), the solution is reintroduced into the main tank, by keeping a constant recirculation. There is a plurality of light emitters (not shown) on the bottom part of the plug (328) that are turned on and off in 12 hours intervals. This is controlled by mean of a Printed Circuit Board within the control module (320). Moreover, there is a stopper, which covers a filling drill hole for the nutritive solution at the bottom part of the liquid containment module (317). The latter was disposed to have a removable element for the removal and introduction of nutritive solution whenever required.

There is a streams exchange module (318) with a streams exchanger cylinder (331) along the axial axe of the main tank (325). The cylinder has a transversal section (preferably circular) with an internal void (332) along its entire axial axe. In a zone next to the top part of the streams exchanger cylinder (331), there is a plurality of bottomless drill holes (333), which allow to constantly keep a nutritive solution at the same level than them, for every time that the nutritive solution falls into the internal void (332). This is because there is a constant recirculation of the nutritive solution caused by the hydraulic pump (324) towards the top part of the main tank (325) as we have mentioned before. Moreover, there is an arrangement of bottomless drill holes (304) distributed at the lower periphery of the streams exchanger cylinder (331). It is here where a polluted stream follows its path after being introduced into the system by mean of a plurality of bottomless drill holes of the storage tank (322).

The module for the capture of gaseous streams (319) is at the top part of the polluted streams purifier bioreactor (315). It is mainly compounded by a gas extractor (335) located on the top part of the main thank (325). Moreover, it is interconnected to the streams exchanger cylinder (331). The polluted streams come from the environment and get into the polluted streams purifier bioreactor (315) by mean of the bottomless drill holes (323) of the storage tank (322). Once the streams have passed through the bottomless drill holes arrangement (323), bioremediation happens in the internal void (322) of the streams exchanger cylinder (331). Finally, there is a gases expulsion cylinder (338) at the top part of the polluted streams purifier bioreactor (315). The latter cylinder has a series of perforations on its periphery to make the treated (bioremediated) gases to go back to the environment where captured before. The gases expulsion cylinder connects to the top part of the main tank (325) by mean of a coupling cylinder (336), which has a partial drill hole on its axial axe, and which imprisons both elements, by keeping them constantly sealed for not allowing the introduction of external elements.

Figure 27:
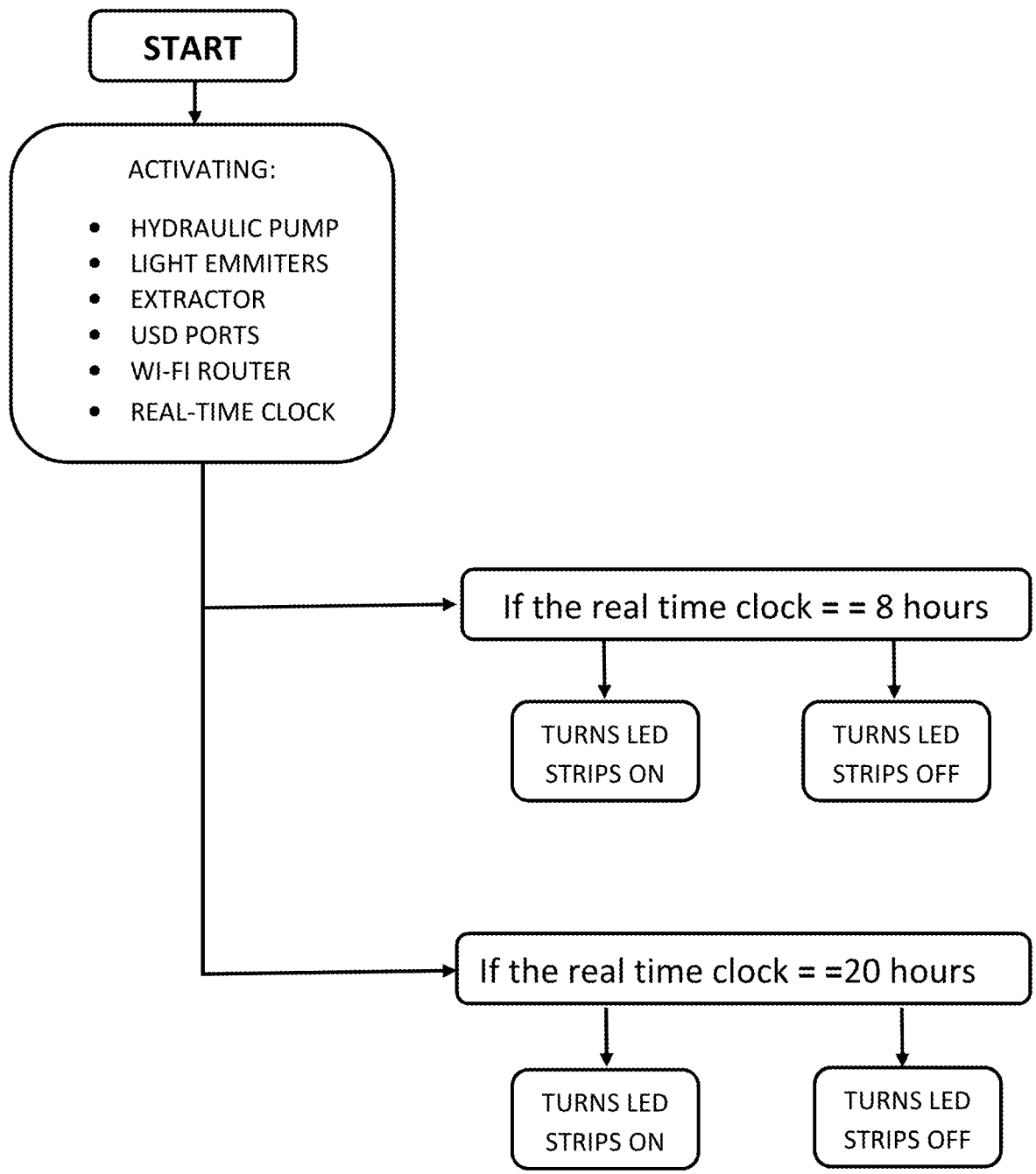
FIG. 27 shows the block diagram of the controller of the Printed Circuit Board.

The control module (320) of the polluted streams purifier bioreactor has a Printed Circuit Board (337). The latter is the element, which not only controls the light emitters turning on and off, but also the switching-on of the hydraulic pump (324) and the air extractor (335). Moreover, it energizes a series of USB ports, a WI-FI router and real-time clock as is shown in FIG. 27.

In a preferential (and optional) modality, the module for the capture of gaseous streams (319) is able to have a mean for capturing powder (not shown) of at least 2 microns. The mean is compounded by a plurality of steel plates distributed in parallel, and alternated with positive and negative charges by mean of drill holes, which horizontally cross the bottom and top parts of the plates. The latter cause negative and positive charges, in a way in which a magnetic field is created in order to separate particles by charges polarity. Each plate is separated by an insulating medium, preferably rubber. Finally, the mean for capturing powder particles connects to the power supply.

In another modality, the flow of nutritive solution inside the streams exchanger cylinder (331) goes (optionally) through a water diffuser mean (not shown) of watering can (or rack) character that allows distributing the solution throughout its interior. Furthermore, this invention considers having filter and supporting means biofilter and diffuser panels' kind (not shown) inside the streams exchanger cylinder (331).

Despite the latter description was elaborated taking account of the invention's preferred modalities, the field expert's must considering, that any shape and detail modification will be comprehended within the spirt and scope of the invention. The terms in which this memory has been written should always be considered in a wide (and not-limitative) sense. The materials, shape and description of the elements are subject to change; whenever not involves an alteration of the essential characteristic of the model.

The invention claimed is:

1. A system for capturing and monitoring atmospheric pollutant agents (1) comprising:
    a protection skeleton (100) to cover and protect the entire system;
    a power supply device (200) to provide electric power to the system;
    a gases bioremediation device (300) for capturing and bioremediating gaseous polluted streams that circulate inside the system;
    a control and monitoring device (400) that census and modifies operation parameters in real time;
    at least one particle capture unit (500) that gathers particles that approach the system inside;

wherein the gases bioremediation device (300) has at least one circumferentially disposed polluted streams purifier bioreactor (315); a power supply device, which provides electric power to the components of the polluted streams purifier bioreactor (315); and a base device (316) at the bottom part as a supporting structure to give stability;

the liquid containment device (317) stores the medium/nutritive solution that requires a variety of microalgae/cyanobacteria to grow;

a streams exchange device (318) to provide the elements to allow a stream having a certain level of pollution to be displaced inside the polluted streams purifier bioreactor (315), by having an exchange of the pollutant elements;

a capturing gaseous streams device (319) to introduce polluted streams from the exterior in order to be treated;

the control device (320) controls several functions of the polluted streams purifier bioreactor (315);

the liquid contention device (317) includes a storage tank (322) that contains a nutritive solution, so as a hydraulic pump (324) to boost the nutritive solution to the interior of the main tank (325) by a plurality of drill holes located at a periphery of the liquid contention device;

a streams exchange device (318) with a streams exchanger cylinder (331) along the axial axe of the main tank (325);

wherein the cylinder has a transversal section with an internal void (322) along the entire axial axe;

the streams exchanger cylinder (331) has a plurality of bottomless drill holes (333) in a zone next to its top side for constantly keeping the level of the nutritive solution at a height when precipitating the nutritive solution to the interior of the internal void (322) since there is a continuous recirculation of the nutritive solution, which is boosted by the hydraulic (324) pump towards the top part of the main tank (325);

wherein the protection skeleton (100) has a helical shape, which includes a plurality of sheets (101) having a square shape with rounds at their vertices, the plurality of sheets (101) is located at a bottom part of the protection skeleton (100);

wherein the sheets (101) located from a middle to a top part of the protection skeleton increase their diagonal distance magnitude by 30 cm intervals in ascending order, the sheets (101) located at the middle and a superior part have a 5-10° rotation on its axial axe in respect of the axial axe of the sheets located at the bottom part of each one of them.

2. The system according to claim 1, the power supply device (200) with an energy source includes a plurality of solar panels (201) located on a top part of the protection skeleton, wherein the panels connect to a battery bank (202) that is at a bottom part of the system for monitoring atmospheric polluting agents (1), the battery bank stores the charge coming from the solar panels (201), to be then connected to a power inverter (203), which converts the direct current electric power coming from the panels (201) into alternating current electric power, the alternating current electric power is a supply source of the gaseous stream collector (301), of the monitoring system (400), so as of a plurality of Light-Emitting Diode strips (309) belonging to the gases bioremediation system (300).

3. A system for capturing and monitoring atmospheric pollutant agents (1) comprising:

a protection skeleton (100) to cover and protect the entire system;

a power supply device (200) to provide electric power to the system;

a gases bioremediation device (300) for capturing and bioremediating gaseous polluted streams that circulate inside the system;

a control and monitoring device (400) that census and modifies operation parameters in real time;

at least one particle capture unit (500) that gathers particles that approach the system inside;

wherein the gases bioremediation device (300) has at least one circumferentially disposed polluted streams purifier bioreactor (315); a power supply device, which provides electric power to the components of the polluted streams purifier bioreactor (315); and a base device (316) at the bottom part as a supporting structure to give stability;

the liquid containment device (317) store the medium/nutritive solution that requires a variety of microalgae/cyanobacteria to grow;

a streams exchange device (318) to provide the elements to allow a stream having a certain level of pollution to be displaced inside the polluted streams purifier bioreactor (315), by having an exchange of the pollutant elements;

a capturing gaseous streams device (319) to introduce the polluted streams from the exterior in order to be treated;

the control device (320) controls several functions of the polluted streams purifier bioreactor (315);

the liquid contention device (317) controls several functions of the polluted streams nutritive solution, so as a hydraulic pump (324) to boost the nutritive solution to the interior of the main tank (325) by a plurality of drill holes located at a periphery of the liquid contention device;

a streams exchange device (318) with a streams exchanger cylinder (331) along the axial axe of the main tank (325);

the cylinder has a transversal section with an internal void (322) along the entire axial axe;

the streams exchanger cylinder (331) has a plurality of bottomless drill holes (333) in a zone next to its top side for constantly keeping the level of the nutritive solution at a height when precipitating the nutritive solution to the interior of the internal void (322) since there is a continuous recirculation of the nutritive solution, which is boosted by the hydraulic (324) pump towards the top part of the main tank (325);

wherein the protection skeleton covers a frame (205) that has a particles capture unit on the top part, a plurality of bioreactors (302) are joined by a plurality of coupling brackets (206) in a zone next to the superior part of the frame, wherein the frame (205) includes a medium base (206) located at a middle part that works as a support for a bottom part of the bioreactors that overlap on it, wherein batteries of the battery bank (202), a power inverter, and a storage are located on a plurality of bases located at the bottom part of the frame.

4. The system according to claim 1, wherein a direct current generates an electrical generator destined to transform magnetic flow into electricity by electromagnetic induction.

5. The system according to claim 1, wherein the storage tank includes a nutritive solution having a sterilized formulation of 1:2 p/v relation of vermicomposting diluted in water.

6. The system according to claim 1, wherein the polluted streams purifier bioreactor (315) contains either a monoculture or polyculture of microalgae and/or cyanobacteria of at least one of: *Tetraselmis, Chlamydomonas, Nannochloris, Scenedesmus, Cyanidium, Synechocystis, Spirulina, Dunaliella, Dunaliella, Chlorella, Tetraselmis, Chlamydomonas, Nannochloris, Scenedesmus, Cyanidium, Anabaena, Nostoc,* mixtures of them, or any other of commercial interest.

7. The system according to claim 1, wherein the microalgae/cyanobacteria monoculture or polyculture are formed by native species from the place where the system is installed.

8. The system according to claim 1, wherein each of the polluted streams purifier bioreactors (315) has a pH sensor that keeps communication with the control and monitoring device (400), the pH sensor identifies when the pH parameter is outside a programmed range and sends a signal for a dispenser to manage a base solution that allows to newly stabilizing the parameter.

9. The system according to claim 1, wherein each one of the polluted streams purifier bioreactors (315) has a temperature sensor that communicates with the control and monitoring device (400).

10. The system according to claim 1, wherein the has at least one air quality sensor that is in communication (400) with the control and monitoring device (400) in order to determine the operation conditions.

11. The system according to claim 1, wherein the control and monitoring device (400) includes a power supply (203) connected to the power inverter output, a programmable logic controller, and a set of relays, the device is connected to the air quality sensors.

12. The system according to claim 1, wherein the particles capture unit (500) is located at a top part of the system, wherein the particles capture unit (500) inverts the polarity and attracts the particles, a power inverter of the power supply device (200) supplies power to the particles capture unit.

13. A polluted streams purifier bioreactor (315) comprising:
an energy supply device, which provides electrical energy to components of a polluted streams purifier bioreactor (315);
a base device (316) located at a bottom part to provide support and stability to the system;
a liquid containment device (317) to store a medium that requires a variety of microalgae/cyanobacteria for an optimum growth;
a streams exchange device (318) to provide elements that allow a stream polluted in a certain level to be displaced to the interior of the polluted streams purifier bioreactor (315), by allowing to have an exchange of elements;
a device for capturing of gaseous streams (319), which is the place where the contaminated streams are introduced from an exterior in order to be treated;
a control device (320) to control several functions of the polluted streams purifier bioreactor (315);
the liquid containment device (317) includes a storage tank (322) that contains a nutritive solution, a hydraulic pump (324) send the nutritive solution towards a top part of a main tank (325) by using a plurality of bottomless drill holes (323) disposed on a periphery;
a streams exchange device (318) including a streams exchanger cylinder (331) along the axial axe of the main tank (325), the cylinder has a transversal section with an internal void (332) along the entire axial axe;
a plurality of bottomless drill holes (333) are located in a zone next to the top part of the streams exchanger cylinder (331), to constantly keeping the nutritive solution at the same level, for when the latter falls into the internal void (332);
wherein the device for capturing gaseous streams (319) is at the to part of the polluted streams purifier bioreactor (315), and a gas extractor (335) interconnected to the stream exchanger cylinder (331), the polluted streams come from the environment and pet into the polluted streams purifier bioreactor (315) by bottomless drill holes (323) of the storage tank (322), the streams pass through the bottomless drill holes arrangement (323) and the internal void (322) of the streams exchanger cylinder (331).

14. The bioreactor according to claim 13, wherein there is an expelling gases cylinder (338) at the top part of the polluted streams purifier bioreactor (315), the cylinder has a series of perforations on a periphery for making treated gases to return to the environment.

15. The bioreactor according to claim 13, wherein the polluted streams purifier bioreactor (315) has a coupling cylinder (336) with a partial drill hole on an axial axe that imprisons both elements.

16. The bioreactor according to claim 13, wherein the control device (320) has a printed circuit board (337), the printed circuit board controls light emitters turning on and off and also controls switching-on of the hydraulic pump (324) and an air extractor (335), and energizes a series of USB ports, a WI-FI router, and real time clock.

17. The bioreactor according to claim 13, wherein the device for the capture of gaseous streams (319) optionally have a device for capturing powder, the device for capturing powder includes a plurality of steel plates distributed in parallel, and alternated with positive and negative charges by drill holes that horizontally cross bottom and top parts of the plates.

18. The bioreactor according to claim 13, wherein the streams exchanger cylinder (331) includes a filter and/or a supporting device inside.

* * * * *